United States Patent [19]
Trani et al.

[11] Patent Number: 5,185,320
[45] Date of Patent: Feb. 9, 1993

[54] $O^{56}$-ALKYL DERIVATIVES OF AGLYCONE AND PSEUDO AGLYCONES OF TEICOPLANIN

[75] Inventors: Aldo Trani, Milan; Pierfausto Seneci, Brescia; Pietro Ferrari, Ferriere; Romeo Ciabatti, Novate Milanese, all of Italy

[73] Assignee: Gruppo Lepetit S.p.A., Milan, Italy

[21] Appl. No.: 707,247

[22] Filed: May 22, 1991

Related U.S. Application Data

[62] Division of Ser. No. 499,221, Mar. 26, 1990, abandoned.

[30] Foreign Application Priority Data

Apr. 3, 1989 [EP] European Pat. Off. ........ 89105822.4

[51] Int. Cl.$^5$ .......................... C07K 7/50; C07K 9/00; A61K 37/02
[52] U.S. Cl. .......................................... 514/8; 514/9; 530/317; 530/322
[58] Field of Search ................... 530/317, 322; 514/8, 514/9

[56] References Cited

U.S. PATENT DOCUMENTS

| | | | |
|---|---|---|---|
| 4,239,751 | 12/1980 | Coronelli et al. | 424/118 |
| 4,594,187 | 6/1986 | Strazzolini et al. | 530/332 |
| 4,629,781 | 12/1986 | Strazzolini et al. | 530/317 |
| 4,645,827 | 2/1987 | Malabarba et al. | 530/322 |
| 4,650,855 | 3/1987 | Malabarba et al. | 530/322 |
| 4,698,418 | 10/1987 | Malabarba et al. | 530/317 |

FOREIGN PATENT DOCUMENTS

| | | |
|---|---|---|
| 0218099 | 4/1987 | European Pat. Off. |
| 0290922 | 11/1988 | European Pat. Off. |
| 0301247 | 2/1989 | European Pat. Off. |
| WO88/06600 | 9/1988 | PCT Int'l Appl. |

OTHER PUBLICATIONS

Cram et al., Organic Chemistry, 2nd Edition, McGraw-Hill Book Company, New York, pp. 249-252 (1964).
A. Borghi et al., J. Antibiotics, vol. 37, 615-620, 1984.
C. J. Barna et al., J. Am. Chem. Soc., 1984, 106, 4895-4902.
A. Malabarba et al., J. Antibiotics, 37, 988 (1984).
Zanol et al., Acta of the 17th International Symposium on Chromatography, Vienna, Sep. 25-30, 1988.
A. Malabarba et al., J. Antibiotics, vol. 40, No. 1572 (1987).
A. Malabarba et al., J. Antibiotics, 39, 1430 (1986).

*Primary Examiner*—Y. Christina Chan
*Attorney, Agent, or Firm*—John J. Kolano

[57] ABSTRACT

The present invention is directed to a new class of teicoplanin derivatives, a process for preparing them and their use as pharmaceutically active substances.

6 Claims, No Drawings

$O^{56}$-ALKYL DERIVATIVES OF AGLYCONE AND PSEUDO AGLYCONES OF TEICOPLANIN

CROSS-REFERENCE TO RELATED APPLICATIONS

This is a divisional of application Ser. No. 07/499,221, filed Mar. 26, 1990, and now abandoned.

The present invention is directed to a new class of teicoplanin derivatives, a process for preparing them and their use as pharmaceutically active substances. The teicoplanin derivatives of the invention are represented by the following formula:

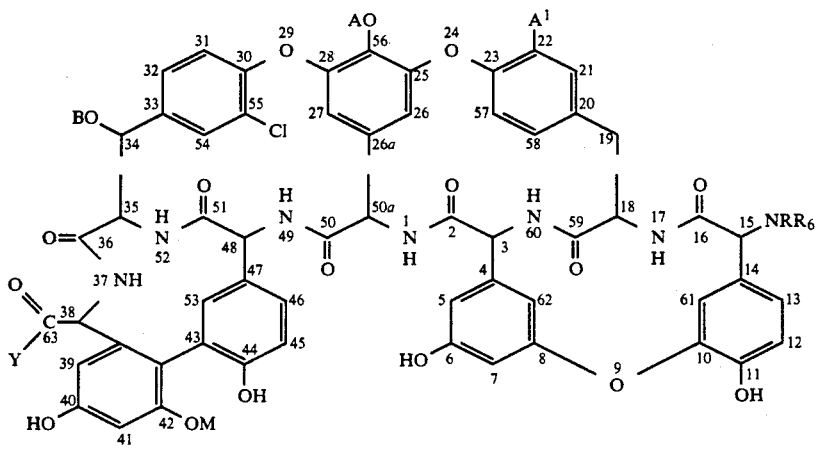

wherein

A represents $(C_1-C_6)$alkyl, $(C_5-C_6)$cycloalkyl, $(C_5-C_6)$ cycloalkyl$(C_1-C_4)$alkyl, $(C_1-C_4)$alkoxy-$(C_1-C_4)$alkyl, hydroxy$(C_1-C_6)$alkyl, epoxy-$(C_3-C_6)$alkyl, 4-7 membered saturated or unsaturated cyclic lactone moieties, halo$(C_1-C_6)$alkyl, cyano$(C_1-C_6)$alkyl, phenyl($C_1-C_4$)alkyl wherein the phenyl ring may be further substituted with a substituent selected from chloro, bromo, iodo, $(C_1-C_3)$alkyl, $(C_1-C_3)$alkoxy, cyano, and hydroxy; a group of formula $(CH_2)_s$ $(CO)_t$—$R^{13}$ wherein one of the hydrogen atoms of a $CH_2$ unit may be replaced by a hydroxy —$(C_1-C_4)$alkyl group, s represents an integer from 1 to 6, t represents zero or 1, and $R^{13}$ represents hydroxy, $(C_1-C_4)$alkoxy or a 5-10 membered saturated, partially unsaturated or aromatic heterocyclic ring containing from 1 to 3 heteroatoms independently selected from nitrogen and oxygen, which may be further substituted on the ring carbons with 1 to 3 groups independently selected from oxo, chloro, bromo, and $(C_1-C_3)$alkyl; or a group of formula

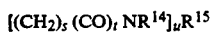

wherein one of the hydrogen atom of a $CH_2$ unit may be replaced by a hydroxy$(C_1-C_4)$alkyl group, s and t are defined as above, u represents an integer from 1 to 6, $R^{14}$ represents a group selected from hydrogen, $(C_1-C_3)$alkyl, $(CH_2)_sNH_2$, $(CH_2)_sNH$ $(C_1-C_2)$alkyl, and $(CH_2)_sN[(C_1-C_2)alkyl]_2$, wherein s is defined as above, and $R^{15}$ represents hydrogen, $(C_1-C_4)$alkyl, $(CH_2)_s$—COO$(C_1-C_4)$alkyl, and $(C_5-C_6)$cycloalkyl;

$A^1$ represents chloro or hydrogen;

R represents hydrogen, $(C_1-C_{12})$alkyl, $(C_4-C_7)$cycloalkyl, cyano $(C_1-C_3)$alkyl, —$(CH_2)_q$—OOC—$(C_1-C_6)$alkyl, wherein q is an integer selected from 1, 2, 3 and 4; or phenyl $(C_1-C_4)$alkyl wherein the phenyl group is optionally substituted in the position ortho, meta and/or para with 1 to 3 groups selected from $(C_1-C_4)$alkyl, nitro, bromo, chloro, iodo, $(C_1-C_4)$alkoxy, and phenyl;

$R^6$ represents hydrogen, $(C_1-C_{12})$alkyl, $(C_4-C_7)$cycloalkyl, cyano $(C_1-C_3)$alkyl, —$(CH_2)_r$—OOC—$(C_1-C_5)$alkyl, wherein r is an integer selected from 1, 2, 3 and 4, phenyl $(C_1-C_4)$alkyl wherein the phenyl group is optionally substituted in the position ortho, meta and/or para with 1 to 3 groups selected from $(C_1-C_4)$alkyl, nitro, bromo, chloro, iodo, $(C_1-C_4)$alkoxy, and phenyl; or $R^6$ represents a group $[CHR^7 (CRR^9)_mX]_n$—$R^{10}$

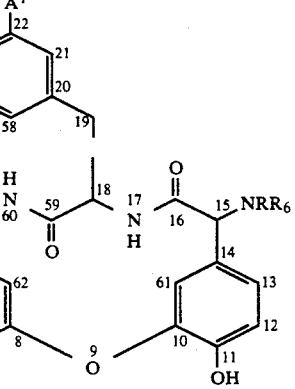

wherein $R^7$ and $R^8$ independently represent H or a $(C_1-C_6)$alkyl;

$R^9$ represents H, a $(C_1-C_6)$alkyl or OH;

$R^{10}$ represents H, a $(C_1-C_3)$alkyl, $COOR^{11}$, $OR^{11}$, $SR^{11}$, $NR^{11}R^{12}$ or halogen;

$R^{11}$ and $R^{12}$ independently represent H or a $(C_1-C_3)$alkyl; m is zero or 1, n is an integer between zero and 6;

X is O, NH or a bond with the proviso that when X is O or NH, then n is different from zero, and $R^9$ is different from OH; with the proviso that when one between R and $R^6$ represents $(CH_2)_n$—OOC—$(C_1-C_6)$alkyl the other must represent hydrogen;

Y represents $OR^{16}$ wherein $R^{16}$ represents hydrogen, halo$(C_1-C_4)$alkyl, hydroxy$(C_1-C_4)$alkyl $(C_1-C_4)$alkyl or phenyl$(C_1-C_4)$alkyl, wherein the phenyl ring may be substituted with 1 to 3 groups selected from $(C_1-C_3)$alkyl, $(C_1-C_3)$alkoxy, chloro, bromo and iodo; a group

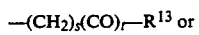

or

wherein these groups are as defined above for the substituent A, or Y represents a group —$NR^1R^2$ wherein $R^1$ represents hydrogen, $(C_1-C_6)$alkyl, hydroxy—$(C_2-C_4)$alkyl, halo$(C_2-C_4)$alkyl, $(C_1-C_4)$alkoxy—$(C_2-C_4)$alkyl, amino$(C_2-C_4)$alkyl, $(C_1-C_4)$alkylamino—$(C_2-C_4)$alkyl, or di$(C_1-C_4)$alkylamino$(C_2-C_2)$alkyl;

$R^2$ represents hydrogen, $(C_1-C_6)$alkyl, hydroxy$(C_2-C_4)$alkyl, halo$(C_2-C_4)$alkyl, $(C_1-C_4)$alkoxy$(C_2-C_4)$alkyl, or a nitrogen containing 5-6 membered heterocyclic ring which may be unsaturated, partially saturated or wholly saturated and may contain 1 to 3 further heteroatoms selected from N, S and O wherein 1 to 3 of the ring carbons may optionally bear $(C_1-C_4)$alkyl sybstituents and one of the nitrogen rings may optionally bear a substituent $R^5$ selected from $(C_1-C_4)$alkyl, $(C_4-C_7)$cycloalkyl, phenyl optionally substituted with halogen or $(C_1-C_4)$alkyl, phenyl $(C_1-C_4)$alkyl, pyridyl, $(C_1-C_4)$alkylpyridinio, and when the ring is wholly saturated two of the ring members may optionally be bridged by an alkylene chain of 1 to 3 carbon atoms wherein one of the methylene groups may optionally be replaced by —NH— or —N[$(C_1-C_4)$alkyl]; a group —alk—W wherein "alk— represents a linear alkylene chain of 1 to 8 carbon atoms which is optionally substituted with a substituent selected from $(C_1-C_4)$alkyl, hydroxy $(C_1-C_4)$alkyl, hydroxy, carboxy aminocarbonyl, $(C_1-C_4)$alkylaminocarbonyl, di$(C_1-C_4)$alkylaminocarbonyl, $(C_1-C_4)$alkylcarbonyl, phenyl $(C_1-C_4)$alkoxycarbonyl, phenyl $(C_1-C_4)$alkoxycarbonyl, and W represents a carboxy, $(C_1-C_4)$alkoxycarbonyl, phenyl $(C_1-C_4)$alkoxycarbonyl, aminocarbonyl, $(C_1-C_4)$alkylaminocarbonyl, di$(C_1-C_4)$alkylaminocarbonyl, ureido, guanidino, a nitrogen containing 5-6 membered heterocyclic ring defined as above, a group of the formula —$NR^3R^4$ wherein $R^3$ and $R^4$ each independently represent hydrogen, $(C_1-C_6)$alkyl, hydroxy$(C_2-C_4)$alkyl and halo$(C_2-C_4)$alkyl or $R^4$ represents phenylmethyloxycarbonyl and $R^3$ represents hydrogen; or $R^1$ and $R^2$ taken together with the adjacent nitrogen atom represent a saturated 5-7 membered heterocyclic ring which may optionally bear one to two $(C_1-C_4)$alkyl substituents on the ring carbons and may contain a further hetero group selected from —O—, —S—, and —$NR^5$— wherein $R^5$ is defined as above;

B represents hydrogen or N-acetyl-beta-D-2-deoxy-2-aminoglucopyranosyl;

M represents hydrogen or alpha-D-mannopyranosyl; with the proviso that when W represents a group —$NR^3R^4$, ureido, guanidino or a nitrogen containing 5-6 membered heterocyclic ring as defined above directly connected with the "alk" moiety through a bond with a ring nitrogen atom, the linear alkylene "alk" moiety must be of at least two carbon atoms; or the pharmaceutically acceptable addition salts thereof.

As used herein the term "alkyl", either alone or in combination with other substituents, includes both straight and branched hydrocarbon groups; more particularly, "$(C_1-C_6)$alkyl" represents a straight or branched aliphatic hydrocarbon chain of 1 to 6 carbon atoms such as methyl, ethyl, propyl, 1-methylethyl, butyl, 1-methylpropyl, 1,1-dimethylethyl, pentyl, 1-methylbutyl, 2-methylbutyl, 1-hexyl, 2-hexyl, 3-hexyl, 3,3-dimethyl-1-butyl, 4-methyl-1-pentyl and 3-methyl-1-pentyl; likewise, "$(C_1-C_4)$alkyl" represents a straight or branched hydrocarbon chain of 1 to 4 carbon atoms such as those alkyl of 1 to 4 carbons exemplified above.

The term "halogen" or "halo" represents a halogen atom selected from fluorine, chlorine, bromine and iodine. "Linear alkylene chains of 1 to 8 carbon atoms" as defined in the present application are straight akylene chains of 1, 2, 3, 4, 5, 6, 7 or 8 carbon atoms. Representative examples of linear alkylene chains of 1 to 6 carbon atoms are:

—$CH_2$—
—$CH_2$—$CH_2$—
—$CH_2$—$CH_2$—$CH_2$—
—$CH_2$—$CH_2$—$CH_2$—$CH_2$—
—$CH_2$—$CH_2$—$CH_2$—$CH_2$—$CH_2$—
—$CH_2$—$CH_2$—$CH_2$—$CH_2$—$CH_2$—$CH_2$—
—$CH_2$—$CH_2$—$CH_2$—$CH_2$—$CH_2$—$CH_2$—$CH_2$—
—$CH_2$—$CH_2$—$CH_2$—$CH_2$—$CH_2$—$CH_2$—$CH_2$—$CH_2$—.

These linear alkylene chain optionally may bear substituents as described above. The expression "a nitrogen containing 5-6 membered heterocyclic ring which may contain 1 to 3 further heteroatoms selected from N, S and O" according to the present invention includes unsaturated, partially saturated and wholly saturated ring systems such as pyridinyl, pyrimidinyl, pyrazinyl, pyrrolidinyl, piperidinyl, piperazinyl, oxazolyl, oxazolinyl, oxazolidinyl, pyrazolinyl, pyrazolidinyl, thiazolidinyl, morpholinyl, thiomorpholinyl, pyrrolyl, pyrrolinyl, imidazoyl, imidazolidinyl, thiadiazolyl, oxadiazolyl, and tetrazolyl, while "5-10 membered heterocyclic ring" includes in addition to the above groups the polycyclic system deriving from the ring condensation of any of the above rings as well as benzo fused ring systems embracing any of the above heterocycles such as benzofuryl, benzopyranyl, benzopyrazolyl, purinyl, indazolyl, indolyl, isoindolyl, indolizinyl, quinolinyl, isoquinolinyl, quinozolinyl, phtheridinyl, and the like, which may be linked to the other part of the moiety as defined above by any available position and preferably by a ring nitrogen. Included in the above definition of 5-10 membered heterocycles are also the corresponding $(C_1-C_4)$alkyl, oxo, chloro and bromo derivatives. A preferred group of this type is 1,3-dihydro-1,3-dioxo-2H-isoindol-2-yl. In said "nitrogen containing 5-6 membered heterocyclic ring" 1 to 3 ring carbons may optionally bear $(C_1-C_4)$alkyl substituents defined as above. When a ring carbon is saturated, it may be simultaneously substituted with two $(C_1-C_4)$alkyl groups. When the above defined "nitrogen containing 5-6 membered heterocyclic ring" is a wholly saturated ring, this definition includes also those heterocyclic rings which have two ring members bridged by an alkylene chain of 1 to 3 carbon atoms wherein a methylene group may optionally be replaced by a group —NH— or —N[($C_1-C_4$)alkyl]. Examples of said bridged rings are the following: 1-azabicyclo[2.2.2]octane, 1,4-diazabicyclo-[3.2.2]nonane, 1-azabicyclo[2.2.1]heptane, 1-azabicyclo[3.2.1]octane, 8-azabicyclo[3.2.1]octane, 3-azabicyclo[3.3.1]octane, 1-azabicyclo[3.3.1]nonane, 9-azabicyclo[3.3.1]nonane, 3,8-diazabicyclo[3.2.1]octane, 2-azabicyclo[2.2.1]heptane, 2-azabicyclo[2.2.2]octane, 3-azabicyclo[3.2.2]nonane.

The expression "a saturated 5-7 membered heterocyclic ring which may optionally bear one to two $(C_1-C_4)$alkyl substituents on the ring carbons and may optionally contain a further heterogroup selected from —O—, —S— and —$NR^5$—" includes, for instance, the following heterocyclic groups: morpholinyl, piperidinyl, piperazinyl, thiomorpholinyl, pyrazolidinyl, 1,3-oxazolidinyl, 1,3-thiazolidinyl and hexahydroazepinyl, which may optionally be substituted by one or two $(C_1-C_4)$alkyl group on the carbon skeleton.

Examples of 4-7 membered saturated or unsaturated cyclic lactone moieties which are encompassed by the present invention are dihydrooxofuryl, tetrahydrooxofuryl, perhydrooxopyranyl, oxooxepyl, and the tautomers thereof and includes in particular residues of the following formulae

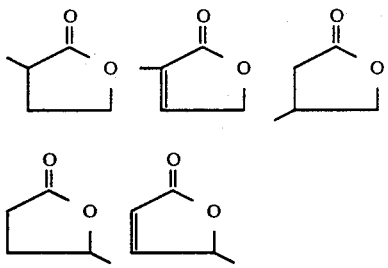

and the tautomers thereof.

A preferred group of compounds of the invention is represented by those compounds of formula I wherein R and $R^6$ represent hydrogen, $A^1$ represents chloro, Y represents hydroxy or represents a group —$NR^1R^2$ wherein $R^1$ represents hydrogen or $(C_1-C_3)$alkyl, $R^2$ represents $(C_1-C_6)$alkyl, a nitrogen containing 5-6 membered heterocyclic ring defined as above wherein 1 to 3 of the ring carbons may optionally bear $(C_1-C_4)$alkyl substituents and one of the ring nitrogens may optionally bear a substituent $R^5$ selected from $(C_1-C_4)$alkyl, $(C_4-C_7)$cycloalkyl, phenyl, and pyridyl; a wholly saturated nitrogen containing 5-6 membered heterocyclic ring which may contain a further nitrogen atom and wherein 1 to 3 of the ring carbons may optionally bear $(C_1-C_4)$alkyl substituents, one of the ring nitrogens may optionally bear a $(C_1-C_4)$alkyl substituent and two of the ring members are bridged by an alkylene chain of 1 to 3 carbon atoms wherein one of the methylene groups may optionally be replaced by —NH— or —N[$(C_1-C_4)$alkyl]; a group —alk—W wherein "alk" represents a linear alkylene chain of 1 to 8 carbon atoms which is optionally substituted with a substituent selected from $(C_1-C_4)$alkyl, carboxy, aminocarbonyl, $(C_1-C_4)$alkylaminocarbonyl, di$(C_1-C_4)$alkylaminocarbonyl, $(C_1-C_4)$alkoxycarbonyl, phenyl$(C_1-C_4)$alkoxycarbonyl, and W represents a carboxy, $(C_1-C_4)$alkoxycarbonyl, phenyl$(C_1-C_4)$alkoxycarbonyl, aminocarbonyl, $(C_1-C_4)$alkylaminocarbonyl, di$(C_1-C_4)$alkylaminocarbonyl, glucosaminocarbonyl, ureido, guanidino, a nitrogen containing 5-6 membered heterocyclic ring which may be unsaturated, partially saturated or wholly saturated and may contain 1 to 3 further heteroatoms selected from N, S and O wherein 1 to 3 of the ring carbons may optionally bear $(C_1-C_4)$alkyl substituents and one of the ring nitrogens may optionally bear a substituent $R^5$ is selected from $(C_1-C_4)$alkyl, $(C_4-C_7)$cycloalkyl, phenyl, and pyridyl; a wholly saturated nitrogen containing 5-6 membered heterocyclic ring which may contain a further nitrogen atom wherein 1 to 3 of the ring carbons may optionally bear $(C_1-C_4)$alkyl substituents, one of the ring nitrogens may optionally bear a substituent $R^5$ representing $(C_1-C_4)$alkyl and two of the ring members are bridged by an alkylene chain of 1 to 3 carbon atoms wherein one of the methylene groups may optionally be replaced by —NH— or —N[$(C_1-C_4$)alkyl]; a group of the formula $NR^3R^4$ wherein $R^3$ and $R^4$ each independently represent hydrogen, $(C_1-C_6)$alkyl, hydroxy$(C_2-C_4)$alkyl and halo$(C_2-C_4)$alkyl, or $R^4$ represents phenylmethyloxycarbonyl and $R^3$ represents hydrogen;

or $R^1$ and $R^2$ taken together with the adjacent nitrogen atom represent a saturated 5-7 membered heterocyclic ring which may optionally bear one to two $(C_1-C_4)$alkyl substituents on the ring carbons and may contain a further heterogroup selected from —O—, —S—, and —$NR^5$— wherein $R^5$ is defined as above;

A is as defined above and B and M either simultaneously represent hydrogen or simultaneously represent the above defined sugar moieties.

A further group of preferred compounds of the invention is represented by those compounds of formula I wherein R and $R^6$ represent hydrogen, $A^1$ represents chloro, Y represents hydroxy or $NR^1R^2$ wherein $R^1$ represents hydrogen or $(C_1-C_4)$alkyl, $R^2$ represents a wholly saturated nitrogen containing 5-6 membered heterocyclic ring which may contain a further nitrogen atom wherein 1 to 3 of the ring carbons may optionally bear $(C_1C_4)$alkyl substituents, one of the ring nitrogens may optionally bear a substituent $R^5$ representing $(C_1-C_4)$alkyl and two of the ring members are bridged by an alkylene chain of 1 to 3 carbon atoms wherein one of the methylene groups may optionally be replaced by —NH— or N[$(C_1-C_4)$alkyl]; or a group —alk—W wherein alk represents a linear alkylene chain of 1 to 3 carbon atoms and W is a wholly saturated nitrogen containing 5-6 membered heterocyclic ring defined as in the paragraph immediately above, B and M either simultaneously represent hydrogen or, simultaneously, represent the above defined sugar moieties and A is defined as above.

A further group of preferred compounds of the invention is represented by those compounds of formula I wherein R and $R^6$ represent hydrogen, $A^1$ represents chloro, Y represents hydroxy or $NR^1R^2$ wherein this group represents —$HNCH(COOCH_3)(CH_2)_4 NH_2$,

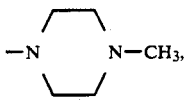

or —HN(alk)W wherein "alk" represents a linear alkylene chain of 2, 3, 4, 5, 6, 7 or 8 methylene units and W represents a group selected from —$NH_2$, —$NHCH_3$, —$NHC_2H_5$, —$N(CH_3)_2$, —$N(C_2H_5)_2$, or —$N(CH_3)(C_2H_5)$, B and M either simultaneously represent hydrogen or simultaneously represent the above defined sugar moieties and A is as defined above.

Another group of preferred compounds of formula I is the one wherein the substituent are as above defined except that Y represents $HN(CH_2)N(CH_3)_2$ and B and M represent hydrogen.

Another group of preferred compounds of the invention is represented by those compounds of formula I above wherein the group represented by A and the one represent by $R^{16}$, for Y equal to $OR^{16}$, are the same.

Examples of preferred meanings for A in formula I above are the following: $(C_5-C_6)$cycloalkyl, $(C_5-C_6)$cycloalkyl $(C_1-C_4)$alkyl, epoxy $(C_3-C_6)$alkyl, hydroxy$(C_2-C_6)$alkyl, $(C_1-C_4)$alkoxy $(C_1-C_4)$alkyl, tetrahydrooxofuryl, halo$(C_2-C_5)$alkyl, cyano$(C_1-C_4)$alkyl, phenyl$(C_1-C_3)$alkyl; a group

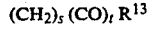

wherein s represents the integer 1, 2, 3 or 4, t represents zero or 1, $R^{13}$ represents hydroxy, $(C_1-C_4)$alkoxy or a 5-10 membered heterocyclic ring selected from morpholinyl, piperidinyl, piperazinyl, pyrrolidyl, indolyl, dioxoindolyl, and oxazolidinyl; a group of formula

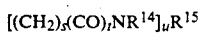

wherein one of the hydrogen atoms of a $CH_2$ may be replaced a hydroxy($C_1$-$C_4$)alkyl group, s represents 2, 3 or 4, t represents zero or 1, u represents 1, 2, 3 or 4, $R^{14}$ represents hydrogen, ($C_1$-$C_3$)alkyl, $(CH_2)_sNH_2$, $(CH_2)_sNH$ ($C_1$-$C_2$)alkyl, $(CH_2)_s$—$N[(C_1$-$C_2)alkyl]_2$, wherein s represents 2, 3 or 4, and $R^{15}$ represents hydrogen, ($C_5$-$C_6$)cycloalkyl, ($C_1$-$C_3$)alkyl or $(CH_2)_s$—$COO(C_1$-$C_3$)alkyl, wherein s represents 2,3 or 4.

Specific examples of groups $(CH_2)_s(CO)_t$ $R^{13}$ included in the meaning of A are the following:

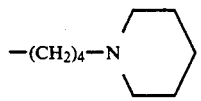
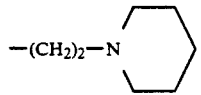
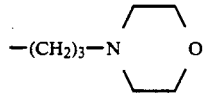

—$(CH_2)COOH$
—$(CH_2)_2COOH$
$CH(CH_2CH_2CH_2OH)COOH$
$CH(CH_2CH_2OH)COOH$

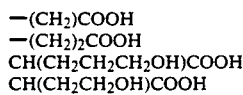
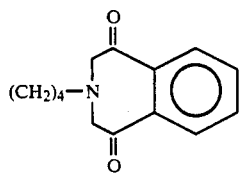
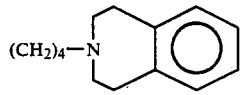
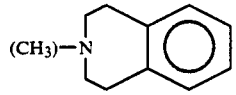

Specific examples of groups $[(CH_2)_s(CO)_t \ R^{14}]_uR^{15}$ included in the meaning of A are the following:

$(CH_2)_4NH_2$ $(CH_2)_2NH(CH_2)_2NH_2$

—$(CH_2)NH(CH_2)_4NH_2$

—$(CH_2)_3NH(CH_4NH(CH_2)_3NH_2$

—$CH_2CONH(CH_2)_3NH(CH_2)_4NH(CH_2)_3NH_2$

—$CH(CH_2CH_2CH_2OH)CO$
   $NH(CH_2)_3NH(CH_2)_4NH(CH_2)_3NH_2$ $(CH_2)_4[N(CH_2)_2 \ N(CH_3)_2]_2$ $CH(CH_2CH_2OH)CONH(CH_2)_2NH_2$ $(CH_2)_2NHCH_2CONHCH_2COOCH_3$ $CH(CH_2CH_2OH)CONHCH_2COOCH_3$ $CH(CH_2CH_2OH)CONH(CH_2)_3 \ N(CH_3)(CH_2)_2CONH_2$

The compounds of the invention can form acid addition salts while those compounds wherein Y is hydroxy can form also base addition salts. When Y is hydroxy and at least one of R' and R'$_6$ is hydrogen also "internal salts" are possible in addition to the "non-salt" form. In this case both the non-salt and the internal salt form are encompassed when dealing with a compound of the invention, unless otherwise specified.

Preferred addition salts of the compounds of this invention are the pharmaceutically acceptable acid and/or base addition salts.

With the term "pharmaceutically acceptable acid and/or base addition salts" are intended those salts with acids and/or bases which from biological, manufacturing and formulation standpoint are compatible with the pharmaceutical practice as well as with the use in the animal growth promotion.

Representative and suitable acid addition salts of the compounds of formula I include those salts formed by standard reaction with both organic and inorganic acids such as, for example, hydrochloric, hydrobromic, sulfuric, phosphoric, acetic, trifluoroacetic, trichloroacetic, succinic, citric, ascorbic, lactic, maleic, fumaric, palmitic, cholic, pamoic, mucic, glutamic, camphoric, glutaric, glycolic, phthalic, tartaric, lauric, stearic, salicylic, methanesulfonic, benzenesulfonic, sorbic, picric, benzoic, cinnamic and the like acids.

Representative examples of these bases are: alkali metal or alkaline earth metal hydroxide such sodium, potassium, and calcium hydroxide; ammonia and organic aliphatic, alicyclic or aromatic amines such as methylamine, dimethylamine, trimethylamine, and picoline.

The transformation of the free amino or non-salt compounds of the invention into the corresponding addition salts, and the reverse, i.e. the transformation of an addition salt of a compound of the invention into the non-salt or free amino form, are within the ordinary technical skill and are encompassed by the present invention.

For instance, a compound of formula I can be transformed into the corresponding acid or base addition-salt by dissolving the non-salt form in an aqueous solvent and adding a slight molar excess of the selected acid or base. The resulting solution or suspension is then lyophilized to recover the desired salt. Instead of lyophilizing, in some instances, it is possible to recover the final salt by extraction with an organic solvent, concentration to a small volume of the separated organic phase and precipitation by adding a non-solvent. In case the final salt is unsoluble in an organic solvent where the non-salt form is soluble it is recovered by filtration from the organic solution of the non-salt form after addition of the stoichiometric amount or a slight molar excess of the selected acid or base.

The non salt form can be prepared from a corresponding acid or base salt dissolved in an aqueous which is then neutralized to free the non-salt form. This is then recovered for instance by extraction with an organic solvent or is transformed into another base or acid addition salt by adding the selected acid or base and working up as above.

When following the neutralization desalting is necessary, a common desalting procedure may be employed. For example, column chromatography on controlled pore polydextrane resins (such as SEPHADEX L H 20) or silanized silica gel may be conveniently used. After eluting the undesired salts with an aqueous solution, the desired product is eluted by means of linear gradient or step-gradient of a mixture of water and a polar or apolar organic solvent, such as acetonitrile/water from 50:50 to about 100% acetonitrile.

As is known in the art, the salt formation either with pharmaceutically acceptable acids (bases) may be used as a convenient purification techniques. After formation and isolation, the salt form of a compound of formula I can be transformed into the corresponding non-salt or into a pharmaceutically acceptable salt.

In some instances the acid addition salt of a compound of formula I is more soluble in water and hydrophilic solvents and has an increased chemical stability. However, in view of the similarity of the properties of the compounds of formula I and their salts, what is said in the present application when dealing with the biological activities of the compounds of formula I applies also to their pharmaceutically acceptable salts, and vice versa.

The compounds of the invention possess antimicrobial activity mainly against gram positive bacteria and can be used as antibiotic active substances. New antibiotics are always in demand to enlarge the therapeutic tools available to improve health care and general welfare by adding active substances with a given antimicrobial spectrum of action, improved potency or selectivity of action, better formulability in pharmaceutical compositions, higher absorption through a given administration route, optimal metabolism and escretion rate or pattern, etc.

Teicoplanin is a complex antibiotic substance obtained by cultivating *Actinoplanes teichomyceticus* ATCC 31101 and is described in U.S. Pat. No. 4,239,751; the single major components of teicoplanin $A_2$ and a process for obtaining them is also known (see A. Borghi et al, J. Antibiotics, Vol. 37, 615–620, 1984; C. J. Barna et al. J. Am. Chem. Soc. 1984, 106, 4895–4902). These components are characterized by having a common heptapepdic nucleus outlined above in formula I. This nucleus is also common and characteristic of all the teicoplanin derivatives described in this application. More particularly, the above mentioned teicoplanin components are represented by the above formula I wherein Y represents hydroxy, R and $R^6$ represent hydrogen, A' represents chloro, A represents —N[($C_{10}$–$C_{11}$)-aliphatic acyl]-beta-D-2-deoxy-2-amino-glucopyranosyl, B represents N-acetyl-beta-D-2-deoxy-2-aminoglucopyranosyl, and M represents alpha-D-mannopyranosyl.

For conciseness, in this description the above referred sugar moieties will be referred to as the "typical sugars" of a given teicoplanin derivative, thus intending that B or M individually represent the above reported sugar moiety.

In teicoplanin $A_2$ component 1, the [($C_{10}$–$C_{11}$)-aliphatic acyl] substituent represents 4-Z-decenoyl, in teicoplanin $A_2$ component 2 represents 8-methyl-nonanoyl, in teicoplanin $A_2$ component 3 represents decanoyl, in teicoplanin $A_2$ component 4 represents 8-methyldecanoyl, in teicoplanin $A_2$ component 5 represents 9-methyldecanoyl.

In the teicoplanin family all the sugar moieties, when present, are linked to the teicoplanin nucleus through O-glycosidic bonds.

Teicoplanin aglycone (i.e. a compound of the above formula wherein Y represents hydroxy, R and $R^6$ represents hydrogen, A, B and M represent hydrogen and $A^1$ represent chloro) and teicoplanin pseudoaglycons (Y represents hydroxy, R and $R^6$ are hydrogens, A, B, and M, are above mentioned typical sugars or hydrogen, provided A, B and M are not all simultaneously hydrogen) are described by A. Malabarba et al. in J. Antibiotics, 37, 988 (1984) 39, 1430 (1986), and EP-A-301247. Carboxy ester derivatives of teicoplanin substances (i.e. compounds of the above formula wherein Y together with the adjacent carbo function represent an ester function and A represents the above reported typical sugar moiety or hydrogen) are described by A. Malabarba et al in J. Antib. 40, 1572 (1987), while carboxyamides (i.e. compounds of the above formula I wherein Y, together with the adjacent carbo function represents a carboxyamide function, and A represents the above reported typical sugar moiety or hydrogen) are described in EP-A-218099, WO88/06600, or EP-A-352538.

Other teicoplanin derivatives differing from the main components of teicoplanin $A_2$ simply in the fatty acid moiety on the glucosamine in position 56 (i.e. the "A" substituent in Formula I) are described in European Patent Application Publication No. 290922 and Zanol et al. Acta of the 17$^{th}$ International Symposium on Chromatography, Vienna, Sep. 25–30, 1988. The above mentioned fatty acid moieties are C-9 and C-12 fatty acids, namely nonanoyl, 6-methyloctanoyl, 10-methylundecanoyl and dodecanoyl.

22-Dechloroteicoplanin derivatives (i.e. compounds of the above formula wherein A is hydrogen or the substituted sugar typical of teicoplanin derivatives and $A^1$ is hydrogen) are described in EP-A-316712 and are obtained by selectively dechlorinating the corresponding 22-chloro compounds preferably in the presence of a suitable reducing agent, such as $PdCl_2/NaBH_4$ in a suitable organic solvent, such as a lower alkanol.

Several processes for converting a teicoplanin derivative into another by selective removal of the sugar units are also described in the art. In particular, processes that can be used to selectively remove the typical sugar represented by B or M in formula I above are described e.g. in EP-A-218099 and 301247.

These processes can be applied to the compounds of the invention wherein B or M or both represent the above mentioned sugar moieties to convert them into other derivatives of the invention wherein B represent the sugar unit and M represent hydrogen or both represent hydrogen.

In general, the compounds of the invention are prepared by alkylating a teicoplanin starting material corresponding to the above formula I, but wherein A represents hydrogen, with an alkylating agent of formula A-Z, according to known per se techniques.

More particularly, the compounds of the invention are preferably prepared by reacting a teicoplanin derivative of formula II

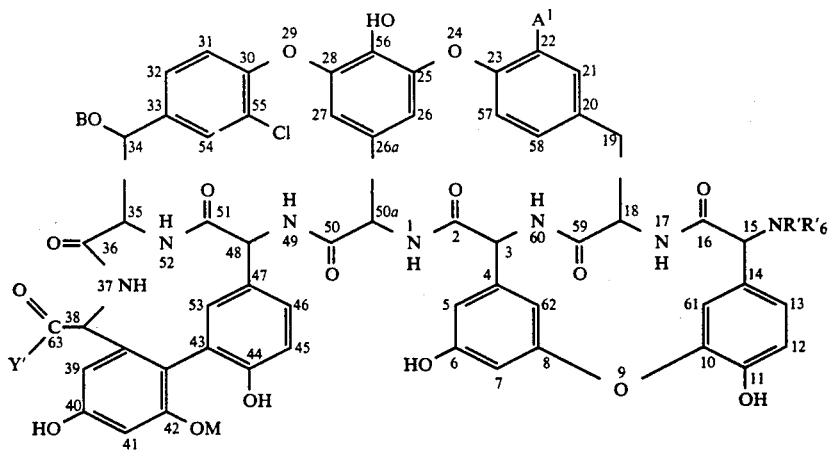

II wherein $A^1$, B, and M are as defined above, Y' includes all the meanings reported above for Y with the exception of hydrogen or Y' represents a protecting group of the carboxy function, R' and $R'_6$ have the meanings reported above for R and $R^6$, or one of R' and $R'_6$ represent hydrogen and the other a protecting group of the amino function with the proviso that R' and $R'_6$ cannot represent simultaneously hydrogen. When Y', R' or $R'_6$ represents a protecting group, the obtained compound is easily deprotected to give compound of formula I above, by means of known per se deprotection procedures. Examples of protecting groups as well as of protection and deprotection procedures will be given below.

A preferred alkylation process is represented by a process wherein a compound of formula II is reacted with an alkylating reagent of formula A-Z, wherein A is defined as above with reference to formula I and Z represents a halogen atom selected from chloro, bromo and iodo, or a good leaving group, in the presence of a base. Examples of good leaving groups that can be used in this process are the conventional ones used in alkylation procedures, such as, preferably, tosyl and mesyl.

One of the preferred Z groups is bromo. Examples of bases are alkali metal and earth-alkali metal hydroxides, such as lithium hydroxyde, sodium hydroxide, potassium hydroxide, and barium hydroxide, alkali metal carbonates, such as sodium or potassium carbonate, ammonia and linear or cyclic organic amines such as triethylamine, trimethylamine, picoline, or morpholine.

An organic cosolvent is oftentimes preferred which is capable of at least partially solubilizing the starting materials. Examples of such a cosolvent are lower alkyl ketones such as acetone, methyl ethyl ketone, and isopropyl methyl ketone, lower alkanols such as methanol, ethanol, propanol; ethers such as tetrahydrofuran and dioxane; lower alkylamides such as dimethylformamide, acetonitrile; sulfoxides such as dimethyl sulfoxide, and their mixtures, including also their aqueous mixtures. Currently, one of the preferred cosolvent is dimethylsulfoxide.

The reaction temperature is generally between room temperature and 80° C., preferably between 30° C. and 70° C. and most preferably about 50° C.

The molar proportion between the starting teicoplanin derivative of formula II and the alkylating agent of formula A-Z can vary within a wide range. Generally, a molar excess of the alkylating agent is preferred to have better yields in the final product. A preferred proportion is from 3 to 50 equivalents of alkylating agent per molar equivalent of teicoplanin starting material, with 5 equivalent being particularly preferred.

Also the molar proportion of the base can vary widely. In general a slight molar excess of the base over the teicoplanin starting material is preferred. Preferably from 1.5 to 5 equivalents of base per molar equivalent of teicoplanin starting material are employed, and most preferably from 2 to 3 molar equivalents.

The reaction process can be monitored according to usual procedures such as by means of TLC or HPLC methods. A preferred analytical procedure is an HPLC method using a commercial apparatus, such as a HEWLETT-PACKARD 1090L, equipped with detector such as a 254 nm UV detector and a reverse-phase silica gel column such as 4.6×100 HIBAR-LICHROSPHER RP-18, 5 micrometers. Elution is carried out at a pre-selected flow-rate, preferably 1 ml/min, and the eluent is a mixture of an aqueous solution with an organic solvent, preferably a linear step gradient mixture of 0.02M aqueous $NaH_2PO_4$ pH 4.8 (eluent a) and acetonitrile (eluent b).

A preferred linear step gradient program for this eluting mixture is the following:

|  |  | Time | 0 | 2 | 25 | 30 | 35 min |
|---|---|---|---|---|---|---|---|
| Method A, | % of b in a: | | 26 | 26 | 40 | 47 | 26 |
| Method B, | % of b in a: | | 35 | 35 | 54 | 54 | 35 |
| Method C, | % of b in a: | | 20 |  |  | 60 | 75 |

According to these techniques, the disappearance of the starting material, the appearance/disappearance of intermediates, or the appearance of the final product, or all these parameters together, may be followed to monitor the reaction course and to decide when the reaction can be considered completed and the recovery of the intermediate/final product may be started.

An example of a preferred process of the invention is represented by a process which comprises dissolving the teicoplanin starting material of formula II in dimethylsulfoxide and then adding potassium carbonate. After stirring at about 40° C. for about 15 min, the mixture is cooled to room temperature and the alkylating agent A-Z is added thereto. After stirring at about 50° C. until the reaction can be considered as complete, the product is recovered according to known per se procedures such as precipitation by adding a precipitating agent (non-solvent), or by concentration and centrifugation, if necessary, extraction with solvents, and the like.

In addition, conventional chromatographic techniques such as liquid-liquid partition chromatography, molar exclusion or affinity chromatography, flash chromatography or preparative HPLC can also be used for purification purposes. All these techniques are as such part of the ordinary knowledge of the skilled technician in this field and need not to be explained in further details.

As mentioned above, in the process of the invention it is preferred that when the starting material is unsubstituted at the 63-carboxy or 15-amino function, these functions are conveniently protected as known per se in the art. This protection avoids the risk of undesired side-reactions and generally is a factor that increases the final yields. Protecting groups of the carboxy or amino functions as well as protecting and deprotecting techniques are known per se in the art and probably need not to be explained in great detail here.

Anyway, the $N^{15}$-amino function can be protected by methods known per se in the art such as those described in reference books such as T. W. Greene, "Protective Groups in Organic Synthesis", John Wiley and Sons, New York, 1981, and M. Mc Omie "Protecting Groups in Organic Chemistry" Plenum Press, New York, 1973. These protecting groups must be stable at the conditions of the reaction process, must not unfavorably interfere with the main reaction, and must be easily cleavable and removable from the reaction medium at the end of the reaction without damaging the newly formed compounds.

Representative examples of N-protecting groups which may be advantageously used in the process of the invention for protecting an amino function of teicoplanin starting material are carbamate forming reagents characterized by the following oxycarbonyl groups: 1,1-dimethylpropynyloxycarbonyl, t-butyloxycarbonyl, vinyloxycarbonyl, aryloxycarbonyl, cinnamyloxycarbonyl, benzyloxycarbonyl, p-nitrobenzyloxycarbonyl, 3,4-dimethoxy-6-nitrobenzyloxycarbonyl, 2,4-dichlorobenzyloxy-carbonyl, 5-benzisoxazolylmethyloxycarbonyl, 9-anthranylmethyloxycarbonyl, diphenylmethyloxycarbonyl, isonicotinyloxycarbonyl, diphenylmethyloxycarbonyl, isonicotinyloxycarbonyl, benzylthiooxycarbonyl, and the like. Other suitable N-protecting agents are aldehydes or ketones, or derivatives thereof which are capable of forming Schiff bases with the amino group of the teicoplanin nucleus to be protected.

Preferred examples of such Schiff base forming agents are benzaldehydes and particularly preferred is 2-hydroxybenzaldehyde (salicylaldehyde). A convenient means of protection in the case the 15-amine is primary, is, at least in some instances the formation of a benzyliden derivative which may be prepared by reacting it with benzaldehyde in a lower alkanol, such as ethanol, preferably at room temperature. After the reaction has been completed, the benzylidene protecting group may be removed has known in the art, e.g. by treating with diluted mineral acid, preferably hydrochloric acid, at room temperature.

Obviously, when the final compound of formula I contains groups which are labile under acidic conditions, e.g. when, B or M represent sugar moieties as above defined which may be hydrolized in a strong acidic medium, other removal conditions must be used, such as catalytic hydrogenation, using for instance Palladium on carbon as the catalyst to remove the proper protecting group.

In this case, however, attention should be paid to the presence of groups which may be modified by catalytic hydrogenation.

As it is appreciated by the skilled technician, the ultimate choice of the specific protecting group depends on the characteristics of the particular derivative which is desired.

Since the conditions of removal of the different protecting groups are known, the skilled technician is capable of selecting the proper protecting group. For instance, where the final compound possess a benzyl ester function or an N-benzyl function, the protecting groups which are usually removable by catalytic hydrogenation, such as the benzyloxycarbonyl group, should be avoided, while those protecting groups which are removable under acidic conditions, such as t.butoxycarbonyl, can be conveniently used. On the contrary, catalytic hydrogenation may be conveniently used in a case like the above when it is desired to convert a compound of formula I containing said N-benzyl or benzyl ester function into the corresponding compound wherein said N-benzyl or benzyl ester function is replaced by a hydrogen atom.

Similarly the known easily removable protecting groups of the carboxylic function are known per se in the art and are reported in reference books such as T. W. Green, Protecting Groups in Organic Synthesis, pages 153-191, 1981, Wiley-Intersciences, N.Y. and the references cited therein.

Examples of such protected group are those capable of forming substituted methyl esters, 2-substituted ethyl esters, substituted benzyl esters, silyl esters, activated esters, stannyl esters, special amides and hydrazides. Specific examples of such protecting groups are those which, upon reaction with a teicoplanin derivative, may represent the following meanings (Y' equal to a O-protecting group in the above formula II): methoxymethyl, methylthiomethyl, tetrahydropyranyl, tetrahydrofuranyl, methoxyethoxymethyl, benzyloxymethyl, phenacyl, p-bromophenacyl, alpha-methylphenacyl, p-methoxyphenacyl, diacylmethyl, N-phthalimidomethyl, ethyl, 2,2,2-trichloroethyl, 2-haloethyl, omega-chloroalkyl, 2-(trimethylsilyl)ethyl, 2-methylthioethyl, 2-(p-Nitrophenylsulfenil)ethyl, 2-(p-toluenesulfonyl)ethyl, 1-methyl-1-phenylethyl, t-butyl, cyclopentyl, cyclohexyl, allyl, cinnamyl, phenyl, p-methylthiophenyl, benzyl, triphenylmethyl, diphenylmethyl, bis(o-nitrophenyl)methyl, 9-anthrylmethyl, 2-(9,10-dioxo)anthrylmethyl, 5-dibenzosuberyl, 2,4,6-trimethylbenzyl, p-bromobenzyl, o-nitrobenzyl, p-nitrobenzyl, p-methoxybenzyl, piperonyl, 4-picolyl, polymer supported benzyl, trimethylsilyl, triethylsilyl t-butyldimethylsilyl, i-propyldimethylsilyl, phenyldimethylsilyl, t-butyl, phenyl, 2-pyridyl, N-hydroxypiperidinyl, N-hydroxysuccinimidoyl, N-hydroxyphthalimidoyl, N-hydroxybenzotriazolyl, O-acyl, oximes, 24-dinitrophenylsulfenyl, 2-alkyl-1,3-oxazolines, 4-alkyl-5-oxo-1,3-oxazolidines, 5-alkyl-4-oxo-1,3-dioxolanes, triethylstannyl, tri-n-butylstannyl.

Some of them, such as the t-butyl, phenyl or 2-pyridyl derivatives may conveniently be in the form of thioesters. Removal of this group is effected, as known in the art, generally under hydrolytic or hydrogenolytic conditions. The obvious pre-requisite for a leaving group to be used in the process of the invention is that of requiring attack and removal conditions that are not destructive of the overall teicoplanin moiety or that negatively interfere with the reaction course of the main process step, i.e. the O-alkylation step.

All the teicoplanin derivatives so far known, such as those mentioned above, can be used in the process of the invention, either directly, if the group A represent a hydrogen atom (or an easily removable protecting group of the hydroxy function), or upon hydrolysis in case the group A represents a sugar moiety as above defined, in order to convert it into a compound of formula II.

This removal of the sugar function in A can be done according to any of the known techniques. Selective conditions for its removal are described for instance in U.S. Pat. No. 4,650,855, U.S. Pat. No. 4,645,827, U.S. Pat. No. 4,594,187, U.S. Pat. No. 4,629,781 and U.S. Pat. No. 4,698,418.

It is also evident that in many instances a compound of the invention may be prepared in more than one way and that a compound of formula I may be transformed into another compound of the invention by known per se reactions.

All these transformations and conversions are evidently encompassed by the scope of the present invention.

In particular, when a derivative of formula I is obtained wherein a halogeno alkyl residue is present, it can be transformed in the corresponding amino substituted derivatives by reacting it with the proper amine; when a derivative of formula I is obtained wherein a lactone function is present, e.g. tetrahydrooxofuryl, it can be converted into the corresponding hydroxyalkyl amide derivative by usual ring opening procedures in the presence of a suitable amine.

The following table reports the structure of some representative compounds of the invention, wherein $A^1$ in formula I represents chloro and $R^1$ and $R^6$ represent hydrogen.

TABLE I

| Compound No. | B | M | Y | A |
|---|---|---|---|---|
| 1 | H | H | $CH_3O$ | 2,3-epoxypropyl |
| 2 | H | H | $CH_3O$ | 4(1,3-dihydro-1,3-dioxo-2H-isoindol-2-yl)butyl |
| 3 | H | H | $CH_3O$ | 1-carboxy-3-hydroxypropyl |
| 4 | H | H | $CH_3O$ | 1-amino-2-ethylaminocarbonyl-3-hydroxypropyl |
| 5 | H | H | $CH_3O$ | 4-aminobutyl |
| 6 | H | H | $CH_3O$ | 4-bis(2,2-dimethylaminoethylamino)butyl |
| 7 | H | H | $CH_3O$ | 2-chloroethyl |
| 8 | H | H | $CH_3O$ | 2-hydroxyethyl |
| 9 | H | H | $CH_3NH$ | 4-aminobutyl |
| 10 | AcGlN | Mann | $CH_3O$ | 4-aminobutyl |
| 11 | H | H | $CH_3O$ | 2-bromoethyl |
| 12 | H | H | $NCCH_2O$ | cyanomethyl |
| 13 | H | H | $CH_3O$ | 2-(1-pyrrolidyl)ethyl |
| 14 | H | H | $CH_3O$ | 2-(1-morpholinyl)ethyl |
| 15 | H | H | $H_2NCH_2CH_2NH$ | 2[(2-aminoethyl)amino]ethyl |
| 16 | H | H | HO | tetrahydro-2-oxo-3-furyl |
| 17 | H | H | $BrCH_2CH_2O$ | 2-bromoethyl |
| 18 | H | H | $BrCH_2CH_2O$ | 2[2[(2-methoxy-2-oxoethyl)amino]-2-oxoethyl]amino]ethyl |
| 19 | H | H | $C_6H_5—CH_2O$ | 2-bromoethyl |
| 20 | H | H | $C_6H_5—CH_2O$ | phenylmethyl |
| 21 | H | H | $C_6H_5CH_2O$ | tetrahydro-2-oxo-3-furyl |
| 22 | H | H | $HOCH_2—CH_2O$ | 2-hydroxyethyl |
| 23 | H | H | —O-tetrahydro-2-oxo-3-furyl | tetrahydro-2-oxo-3-furyl |
| 24 | H | H | ACAECP—O— | AECP |
| 25 | H | H | APAB—O— | APAB |
| 26 | H | H | OH | 2-ethoxy-ethyl |

AcGlN means N-acetyl-beta-D-2-deoxy-2-aminoglucopyranosyl.
Mann means Alfa-D-mannopyranosyl.
AECP means 1[[(2-aminoethyl)amino]carbonyl]-3-hydroxypropyl].
APAB means 1[[[3-(4-[(3-aminopropyl)amino]-butyl]amino]propyl]aminocarbonyl]-3-hydroxypropyl.

The following table reports the structure of some intermediates in the preparation of representative compounds of the invention, together with their retention times ($t_R$) measured with an HPLC apparatus HEWLETT-PACKARD 1090L, equipped with a 254 nm UV detector and a reverse-phase silica gel column 4.6 × 100 HIBAR-LICROSPHER RP-18, 5 micrometers, eluting at a flow-rate of 1 ml/min, and using a linear step gradient mixture of 0.02M aqueous $NaH_2PO_4$ pH 4.8 (eluent a) and acetonitrile (eluent b) as the eluent, according to one of the following two procedures:

| | | Time | 0 | 2 | 25 | 30 | 35 min |
|---|---|---|---|---|---|---|---|
| Method A, | % of b in a: | | 26 | 26 | 40 | 47 | 26 |
| Method B, | % of b in a: | | 35 | 35 | 54 | 54 | 35 |
| Method C | % of b in a: | | 20 | | | 60 | 75 |

The compounds reported below are represented by the above formula II wherein $A_1$ and $R'_1$ represent hydrogen and the other substituents have the meanings reported below:

TABLE II

| Intermediate No. | M | B | $R'_6$ | Y | A | $t_R$ |
|---|---|---|---|---|---|---|
| III | H | H | BOC | OH | H | 6.8(A) |
| IV | H | H | CBZ | OH | H | 8.2(A) |
| V | H | H | CBZ | $OCH_3$ | H | 8.0(B) |
| VI | H | H | BOC | $OCH_3$ | H | 5.8(B) |

TABLE II-continued

| Intermediate No. | M | B | R'₆ | Y | A | $t_R$ |
|---|---|---|---|---|---|---|
| VII | H | H | BOC | OCH₂CN | H | 23.2(A) |
| VIII | H | H | BOC | NHCH₃ | H | 3.8(B) |
| IX | Mann | AcGlN | CBz | OCH₃ | H | 13.5(B) |
| X | H | H | BOC | OCH₂CH₂Br | H | 20.2(B) |
| XI | H | H | BOC | OCH₂C₆H₅ | H | |
| XII | H | H | CBz | OCH₃ | tetrahydro-2-oxo-furanyl | 19.0(B) |
| XIII | H | H | CBz | OCH₃ | 2,3-epoxypropyl | 13.0(B) |
| XIV | H | H | CBz | OCH₃ | 4(1,3-dihydro-1,3-dioxo-2H-isoindol-2-yl)butyl | 21.0(B) |
| XV | H | H | CBz | OCH₃ | 1-[[2-aminoethylamino]carbonyl]3-hydroxypropyl | 16.0(A) |
| XVI | H | H | CBz | OCH₃ | 4-aminobutyl | 21.0(A) |
| XVII | H | H | BOC | OCH₃ | 2-hydroxyethyl | |
| XVIII | H | H | BOC | NHCH₃ | 4(1,3-dihydro-1,3-dioxo-2H-isoindol-2-yl)butyl | 15.0(B) |
| XIX | H | H | BOC | NHCH₃ | 4-aminobutyl | 7.0(B) |
| XX | H | H | BOC | OCH₃ | 2-chloroethyl | 21.0(B) |
| XXI | H | H | CBz | OCH₃ | 4-bis(2,2-dimethylamino-ethylamino)butyl | 18.0(B) |
| XXII | Mann | AcGlN | CBz | OCH₃ | 4(1,3-dihydro-1,3-dioxo-2H-isoindol-2-yl)butyl | 27.5(A) |
| XXIII | Mann | AcGlN | CBz | OCH₃ | 4-aminobutyl | 12.0(A) |
| XXIV | H | H | BOC | OCH₂CN | CH₂CN | 16.0(B) |
| XXV | H | H | CBz | OCH₃ | 2-bromoethyl | 21.0(B) |
| XXVI | H | H | CBz | OCH₃ | 2-(1-pyrrolidyl)ethyl | 11.5(B) |
| XXVII | H | H | CBz | OCH₃ | 1-morpholinoethyl | 10.5(B) |
| XXVIII | H | H | BOC | NH—CH₂CH₂NHBOC | H | 25.5(A) |
| XXIX | H | H | BOC | NH—CH₂CH₂NHBOC | 2-bromoethyl | 22.5(B) |
| XXX | H | H | BOC | NH—CH₂CH₂NHBOC | 2(2-aminoethylamino)ethyl | 7.5(B) |
| XXXI | H | H | BOC | O—CH₂CH₂Br | 2-bromoethyl | 27.5(C) |
| XXXII | H | H | BOC | O—CH₂CH₂Br | CH₂)₂—(NHCH₂—CO)₂OCH₃ | 27.0(C) |
| XXXIII | H | H | BOC | OCH₂C₆H₅ | CH₂C₆H₅ | 36.0(C) |
| XXXIV | H | H | BOC | O—CH₂CH₂OH | 2-hydroxyethyl | 22.0(C) |
| XXXV | H | H | BOC | OCH₂C₆H₅ | 2-bromoethyl | 28.5(C) |
| XXXVI | H | H | BOC | OCH₂C₆H₅ | tetrahydro-2-oxo-3-furyl | 25.5(C) |
| XXXVII | H | H | BOC | tetrahydro-2-oxo-3-furyl | tetrahydro-2-oxo-3-furyl | 24.0(C) | wherein
Mann means Alfa-D-mannopyranosyl.
AcGlN means N-acetyl-beta-D-2-deoxy-2-aminoglucopyranosyl.
BOC means t.butyloxycarbonyl
CBz means benzyloxycarbonyl The mass spectral data (MS) relating to some representative compounds of the invention obtained on a KRATOS MS-50 spectrometer equipped with a standard FAB source and a high-field magnet, after having dissolved the sample in a mixture of monothioglycerol and calibrated the mass range by using a mixture of CsI and NaI as the reference system are reported below together with the HPLC retention time ($t_R$) determined with the instrument and procedures described above:

| Compound no. | MW | Formula | $t_R$ |
|---|---|---|---|
| 1 | 1269.33 | C₆₂H₅₁N₇O₁₉Cl₂ | 8.2(A) |
| 2 | 1414.19 | C₇₁H₅₈N₈O₂₀Cl₂ | 20.0(A) |
| 3 | 1351.51 | C₆₃H₅₃N₇O₂₁Cl₂.HCl | 12.5(A) |
| 4 | 1430.05 | C₆₅H₅₉N₉O₂₀Cl₂.2HCl | 2.5(A) |
| 5 | 1357.01 | C₆₃H₅₆N₈O₁₈Cl₂.2HCl | 3.4(A) |
| 6 | 1426.37 | C₇₁H₇₄N₁₀O₁₈Cl₂ | 11.4(A) |
| 7 | 1275.5 | C₆₁H₅₀N₇O₁₈Cl₃ | 15.2(A) |
| 8 | 1257.08 | C₆₁H₅₁N₇O₁₉Cl₂ | 3.8(A) |
| 9 | 1283.05 | C₆₃H₅₇N₉O₁₇Cl₂ | 2.6(A) |
| 11 | 1319.91 | C₆₁H₅₀N₇O₁₈BrCl₂ | 12.5(A) |
| 12 | 1391.03 | C₆₂H₄₇N₉O₁₈Cl₂ CF₃COOH | 11.6(A) |
| 13 | 1383.04 | C₆₅H₅₈N₈O₁₈Cl₂.2HCl | 5.4(A) |
| 14 | 1399.04 | C₆₅H₅₈N₈O₁₉Cl₂.2HCl | 4.2(A) |
| 15 | 1343.24 | C₆₄H₆₁N₁₁O₁₈Cl₂ | |

-continued

| Compound no. | MW | Formula | $t_R$ |
|---|---|---|---|
| 16 | 1283.01 | C₆₂H₄₉N₇O₂₀Cl₂ | 13.0(C) |
| 17 | 1412.8 | C₆₂H₅₁N₇O₁₈Br₂Cl₂ | 26.5(C) |
| 18 | 1478.07 | C₆₇H₆₀N₉O₂₁BrCl₂ | 25.0(C) |
| 19 | 1464.13 | C₇₂H₆₂N₇O₁₈BrCl₂ | 31.0(C) |
| 20 | 1379.18 | C₇₂H₅₇N₇O₁₈Cl₂ | 10.0(C) |
| 21 | 1373.13 | C₆₉H₅₅N₇O₂₀Cl₂ | 13.5(C) |
| 22 | 1287.04 | C₆₂H₅₃N₇O₂₀Cl₂ | 25.0(C) |
| 23 | 1367.08 | C₆₆H₅₃N₇O₂₂Cl₂ | 22.5(C) |
| 24 | 1487.28 | C₇₀H₆₉N₁₁O₂₂Cl₂ | 19.0(C) |
| 25 | 1771.78 | C₈₆H₁₀₅N₁₅O₂₂Cl₂ | 18.5(C) |
| 26 | 1385.13 | C₆₂H₅₃O₁₉N₇Cl₂ | 3.4(A) |

The following table reports the H¹NMR data obtained at 500 MHz with a BRUKER AM-500 spectrometer in DMSO-d₆ with tetramethylsilane (TMS) as the internal reference (delta; 0.0 ppm). Chemical shift assignment for each individual resonance are made on the basis of two-dimensional correlation spectroscopy (COSY) by analogy to the parent glycopeptide and/or its aglycone followed by two dimensional nuclear Overhauser analysis (NOESY). The spectral patterns pointed out a substitution in position $O^{56}$ of the teicoplanin nucleous.

TABLE III

| Compound No. | ¹H NMR Spectra (delta, ppm) in DMSO-d₆ (proton attribution) |
|---|---|
| 1 | 7.81 (C₅₄—H); 6.10 (C₃₉—H); 5.70 (C₅₀ₐ—H); 5.55 (C₂₅—H) (C₁₅—H); 5.38 (C₃—H); 5.17, (C₂₇—H); 5.12 (C₃₄—H); 4.91 (C₁₈—H); 4.53 (C₃₈—H); 4.35 (C₄₈—H); 3.72 |

TABLE III-continued

| Compound No. | $^1$H NMR Spectra (delta, ppm) in DMSO-d$_6$ (proton attribution) |
|---|---|
| | (OCH$_3$); 4.29-3.30 (CH$_2$) and (CH) of epoxide, (CH$_2$O—C$_{56}$) |
| 2 | 10.0-9.0 (phenolic OH's); 7.80 (phtalimide CH's); 6.07 (C$_{39}$—H); 5.67 (C$_{50a}$—H); 5.52 (C$_{25}$—H); 5.49 (C$_{15}$—H); 5.36 (C$_3$—H); 5.11 (C$_{27}$—H); and (C$_{34}$—H); 4.89 (C$_{18}$—H); 4.49 (C$_{38}$—H); 4.35-4.20 (CH$_2$O—C$_{56}$), (C$_{48}$—H); 3.69 (OCH$_3$); 1.83 (CH$_2$) of the aliphatic chain) |
| 3 | 8.55 (N$_{49}$—H), (N$_{37}$—H); 7.78 (C$_{54}$—H); 6.06 (C$_{39}$—H); 5.68 (C$_{50a}$—H); 5.48 (C$_{25}$—H); 5.33 (C$_3$—H); 5.09 (C$_{27}$—H) and (C$_{34}$—H); 4.89 (C$_{18}$—H); 4.47 (C$_{38}$—H); 4.30 (C$_{48}$—H); 5.09 (—CH—); 3.7 (—CH$_2$OH); 2.08 (—CH$_2$—); 3.68 (OCH$_3$) |
| 4 | 10.5-8.98 (phenolic OH's); 6.06 (C$_{39}$—H); 5.66 (C$_{50a}$—H); 5.51 (C$_{25}$—H); 5.34 (C$_3$—H); 5.11 (C$_{27}$—H) and (C$_{34}$—H); 5.10 (—CH$_2$—OH); 3.7 (—CH$_2$OH); 2.10 (—CH$_2$); 4.83 (C$_{18}$—H); 4.48 (C$_{38}$—H); 4.33 (C$_{48}$—H); 4.12 (C$_{35}$—H); 3.68 (OCH$_3$); 2.83 (CH$_2$—NH$_2$) |
| 5 | 9.92-8.88 (phenolic OH's); 6.10 (C$_{39}$—H); 5.68 (C$_{50a}$—H); 5.56 (C$_{25}$—H); 5.39 (C$_3$—H); 5.19 (C$_{27}$—H); 5.12 (C$_{34}$—H); 4.54 (C$_{38}$—H); 4.34 (C$_{48}$—H); 4.13 (C$_{35}$—H); 4.25 (CH$_2$-1); 1.89 (CH$_2$-1, CH$_2$-3); 2.92 (CH$_2$-4); 3.71 (OCH$_3$) |
| 6 | 6.08 (C$_{39}$—H); 5.68 (C$_{50a}$—H); 5.55 (C$_{25}$—H); 5.38 (C$_3$—H); 5.17 (C$_{27}$—H); 5.11 (C$_{34}$—H); 4.88 (C$_{18}$—H); 4.52 (C$_{38}$—H); 4.26 (CH$_2$-1); 1.85 (CH$_2$-2), (CH$_2$-3); 2.78 (N—CH$_2$); 2.51 (N—CH$_3$); 4.13 (C$_{35}$—H); 3.70 (OCH$_3$) |
| 7 | 10.20-9.03 (phenolic OH's); 6.08 (C$_{39}$—H); 5.72 (C$_{50a}$—H); 5.52 (C$_{25}$—H); 5.38 (C$_3$—H); 5.17 (C$_{27}$—H); 5.11 (C$_{34}$—H); 4.91 (C$_{18}$—H); 4.50 (C$_{38}$—H); 4.50 (OCH$_2$); 4.00 (CH$_2$Cl); 3.71 (OCH$_3$) |
| 8 | 9.48-8.81 (phenolic OH's); 6.10 (C$_{39}$—H); 5.65 (C$_{50a}$—H); 5.59 (C$_{15}$—H); 5.50 (C$_{25}$—H); 5.38 (C$_3$—H); 5.16 (C$_{27}$—H); 5.11 (C$_{34}$—H); 4.91 (C$_{18}$—H); 4.53 (C$_{38}$—H); 4.34 (C$_{48}$—H); 4.12 (C$_{35}$—H); 4.25 (OCH$_2$); 3.81 (CH$_2$OH); 3.70 (OCH$_3$) |
| 9 | 6.23 (C$_{39}$—H); 5.77 (C$_{50a}$—H); 5.58 (C$_{25}$—H); 5.39 (C$_3$—H); 5.29 (C$_{34}$—H); 5.21 (C$_{27}$—H); 4.95 (C$_{18}$—H); 4.38 (C$_{38}$—H); 4.26 (OCH$_2$); 1.88 (CH$_2$-2, (CH$_2$-3); 2.91 [CH$_2$(NH$_2$)]; 2.70 [CH$_3$(NH)] |
| 10 | 6.49-6.23 (C$_{39}$—H); (C$_{41}$—H); (C$_5$—H); (C$_7$—H); (C$_{62}$—H); 5.68 (C$_{50a}$—H); 6.61 (C$_{25}$—H); 5.26 (C$_{34}$—H); 5.14 (C$_{27}$—H); 4.65 (C$_{18}$—H); 4.57 (C$_{38}$—H); 4.25 (anomeric proton of acetylglucosamine, (C$_4$—OCH$_2$); 3.70 (OCH$_3$); 2.86 [ CH$_2$(NH$_2$)]; 1.88 (CH$_3$—CO); 1.84 (CH$_2$—CH$_2$) |
| 11 | 6.05 (C$_{39}$—H); 5.75 (C$_{50a}$—H); 5.70 (C$_{25}$—H); 5.32 (C$_3$—H); 5.12 (C$_{27}$—H); 5.10 (C$_{34}$—H); 4.97 (C$_{18}$—H); 4.54 (C$_{38}$—H), (OCH$_2$); 4.32 (C$_{48}$—H); 4.12 (C$_{35}$—H); 3.84 (CH$_2$Br); 3.68 (OCH$_3$) |
| 12 | 9.96-9.07 (phenolic OH's); 7.78 (C$_{54}$—H); 6.07 (C$_{39}$—H); 5.75 (C$_{50a}$—H); 5.55 (C$_{25}$—H); 5.40-5.09 (C$_3$—H); (C$_{27}$—H); (COOCH$_2$—CN); (C$_{56}$—OCH$_2$CN); 4.93 (C$_{18}$—H); 4.53 (C$_{38}$—H); 4.32 (C$_{48}$—H); 4.12 (C$_{35}$—H); 2.86 (C$_{19}$—H); |
| 13 | 10.0-9.45 (phenolic OH's); 7.80 (C$_{54}$—H); 6.07 (C$_{39}$—H); 5.69 (C$_{50a}$—H); 5.60 (C$_{25}$—H); 5.57 (C$_{15}$—H); 5.37 (C$_3$—H); 5.17 (C$_{27}$—H); 5.10 (C$_{34}$—H); 4.86 (C$_{18}$—H); 4.60 (C$_{56}$—OCH$_2$); 4.50 (C$_{38}$—H); 4.33 (C$_{48}$—H); 4.11 (C$_{35}$—H); 3.70 (OCH$_3$); 3.65 (N—CH$_2$ pyrrolidine); 2.92 (C$_{19}$—H); 1.99, 1.88 (CH$_2$ pyrrolidine) |
| 14 | 9.98-8.96 (phenolic OH's); 6.06 (C$_{39}$—H); 5.70 (C$_{50a}$—H); 5.56 (C$_{25}$—H); 5.37 (C$_3$—H); 5.16 (C$_{27}$—H); 5.10 (C$_{34}$—H); 4.86 (C$_{18}$—H); 4.65 (CH$_2$O—C$_{56}$); 4.50 (C$_{38}$—H); 4.32 (C$_{48}$—H); 4.10 (C$_{35}$—H); 4.0-3.6 (morpholine CH$_2$); 3.68 (OCH$_3$); 2.90 (C$_{19}$—H); |
| 15 | 7.79 (C$_{54}$—H); 6.20 (C$_{39}$—H); 5.71 (C$_{50a}$—H); 5.54 (C$_{25}$—H); 5.43 (C$_{15}$—H); 5.39 (C$_3$—H); 5.25 (C$_{34}$—H); 5.18 (C$_{27}$—H); 4.92 (C$_{18}$—H); 4.24 (C$_{56}$—OCH$_2$) and (C$_{38}$—H); 4.36 (C$_{48}$—H); 4.15 (C$_{35}$—H); 3.5-2.9 (various NCH$_2$) |
| 16 | 8.48-6.21 (aromatic protons, peptidic NH's); 5.72-4.11 (peptidic CH); 5.82, 4.39 (CH, CH$_2$ lactone) |
| 17 | 9.90-9 (phenolic OH's); 8.56-6.10 (aromatic protons, peptidic NH's) 4.13-5.65 (peptidic CH's); 4.53, 4.44, 3.84, 3.66 (CH$_2$, side chains) |
| 18 | 9.85-9.0 (phenolic OH's) 8.52-6.13 (aromatic protons, peptidic NH's); 4.13-5.62 (peptidic CH's); 4.38, 4.10 (CH$_2$ CH$_2$ R$_2$) 4.42, 4.95, 3.5 (CH$_2$ - side chains) |
| 19 | 9.98-9.90 (phenolic OH's); 8.5-6.1 (aromatic protons, peptidic NH's) 5.70-4.05 (peptidic CH's); 5.18 (CH$_2$ benzyl); 4.55, 3.85 (CH side chains) |
| 20 | 9.98-9.0 (phenolic OH's); 8.5-6.14 (aromatic protons, peptidic NH's) 5.65-4.08 (peptidic CH's); 5.32, 5.14 (CH$_2$ benzyl) |
| 21 | 8.5-6.12 (aromatic protons, peptidic NH's); 5.68-4.08 (peptidic CH's); 5.12 (CH$_2$-benzyl); 5.72, 4.53 (CH, CH$_2$-lactane) |
| 22 | 8.52-6.09 (aromatic protons, peptidic NH's), 5.53-4.12 (peptidic CH's); 4.23, 3.78, 3.58, (CH$_2$ side chains) |
| 23 | 9.98-9.0 (phenolic OH's); 8.53-6.11 (aromatic protons, peptidic NH's); 5.68-4.08 (peptidic CH's); 5.65, 5.15, 4.43, 4.35, (CH, CH$_2$-acetone) |
| 24 | 8.55-6.08 (aromatic protons, peptidic NH's); 5.75-4.10 (peptidic CH's) 3.78, 3.12, 3.08, 2.18 (CH$_2$-side chains) |
| 25 | 8.52-6.05 (aromatic protons, peptidic NH's); 5.58-4.13, (peptidic CH's), 3.85, 3.72, 3.28, 2.12, 1.75, 1.55 (CH$_2$ side chains) |
| 26 | 10.01-8.96 (phenolic OH's); 7.79 (C$_{54}$—H); 6.24 (C$_{39}$—H); 5.71 (C$_{50a}$—H); 5.52 (C$_{25}$—H); 5.37, (C$_3$—H); 5.14 (C$_{27}$—H); 5.09 (C$_{34}$—H); 4.89, (C$_{18}$—H); 4.41 (C$_{38}$—H); 4.33 (C$_{48}$—H, C$_{56}$—O—CH$_2$—); 4.12, (C$_{35}$—H); 3.79, (O—CH$_2$—(CH$_2$)); 3.55 (CH$_2$)—(CH$_3$)); 2.93, (C$_{19}$—H); 1.12, (CH$_3$—(CH$_2$)) |

The antibacterial activity of the compounds of the invention can be demonstrated in vitro by means of standard agar-dilution tests.

ISOSENSITEST broth (Oxoid) and TOLLD-HEWITT broth (Difco) are used for growing staphylococci and streptococci, respectively. Broth cultures are diluted so that the final inoculum is about 10$^4$ colony forming units/ml (CFU/ml). Minimal inhibitory concentration (MIC) is considered as the lowest concentration which shows no visible growth after 18-24 h incubation at 37° C. The results of the antibacterial testing of representative compounds of formula I are summarized in the following Table IV:

TABLE IV

| | Compound No. | | | | | |
|---|---|---|---|---|---|---|
| | 1 | 2 | 3 | 4 | 5 | 6 |
| Staph. aureus Tour L 165 | 0.125 | 2 | 0.5 | 0.125 | 0.125 | 0.25 |
| Staph. haemolyticus L 602 | 1 | 4 | 2 | 0.5 | 0.5 | 0.5 |
| Staph. epidermidis ATCC 12228 | 0.063 | 2 | 0.25 | 0.125 | 0.125 | 0.25 |
| Strep. pyogenes C 203 | 0.063 | 0.125 | 0.125 | 0.063 | 0.063 | 0.032 |
| Strep. pneumoniae UC41 | 0.125 | 0.125 | 0.125 | 0.125 | 0.125 | 0.25 |
| Strep. faecalis ATCC 7080 | 0.5 | 4 | 0.125 | 0.25 | 0.125 | 0.5 |
| Strep. mitis L 796 | 0.25 | 0.125 | 0.25 | 0.125 | 0.125 | 0.125 |
| Neisseria gonorrhoeae ISM68/126 | 64 | >128 | 64 | 64 | n.d. | 128 |
| Haemophilus influenzae ATCC 19418 | 64 | >128 | >128 | 128 | n.d. | |
| Escherichia coli SKF 12140 | 32 | >128 | >128 | 16 | 8 | 16 |
| Proteus vulgaris ATCC 881 | 64 | >128 | >128 | 128 | 32 | >128 |
| Pseudomonas aeruginosa ATCC 10145 | >128 | >128 | >128 | 64 | 32 | >128 |

| | Compound No. | | | | | |
|---|---|---|---|---|---|---|
| | 7 | 8 | 9 | 10 | 11 | 12 |
| Staph. aureus Tour L 165 | 0.125 | 0.125 | 0.25 | 2 | 0.5 | 0.125 |
| Staph. haemolyticus L 602 | 1 | 2 | 0.25 | 16 | 2 | 1 |
| Staph. epidermidis ATCC 12228 | 0.5 | 0.125 | 0.125 | 4 | 0.125 | 0.063 |
| Strep. pyogenes C 203 | 0.125 | 0.063 | 0.063 | 0.125 | 0.125 | 0.125 |
| Strep. pneumoniae UC41 | 0.125 | 0.125 | 0.125 | 1 | 0.25 | 0.125 |
| Strep. faecalis ATCC 7080 | 2 | 0.125 | 0.125 | 4 | 1 | 1 |
| Strep. mitis L 796 | 0.25 | 0.125 | 0.125 | 1 | 0.25 | 0.125 |
| Neisseria gonorrhoeae ISM68/126 | >128 | 32 | 64 | >128 | >128 | >128 |
| Haemophilus influenzae ATCC 19418 | 64 | 64 | 64 | >128 | 64 | 64 |
| Escherichia coli SKF 12140 | >128 | 32 | 8 | >128 | 64 | >128 |
| Proteus vulgaris ATCC 881 | >128 | >128 | 32 | >128 | >128 | >128 |
| Pseudomonas aeruginosa ATCC 10145 | >128 | >128 | 64 | >128 | >128 | >128 |

| | Compound No. | | | | | |
|---|---|---|---|---|---|---|
| | 13 | 14 | 15 | 16 | 17 | 18 |
| Staph. aureus Tour L 165 | 0.125 | 0.25 | 0.125 | 0.125 | 0.25 | 0.13 |
| Staph. haemolyticus L 602 | 0.5 | 2 | 0.25 | 4 | 4 | 2 |
| Staph. epidermidis ATCC 12228 | 0.25 | 0.125 | 0.125 | 0.25 | 0.125 | |
| Strep. pyogenes C 203 | 0.125 | 0.25 | 0.063 | 0.5 | 0.125 | 0.125 |
| Strep. pneumoniae UC41 | 0.25 | 0.125 | 0.125 | 0.25 | 0.5 | |
| Strep. faecalis ATCC 7080 | 0.125 | 0.125 | 0.25 | 0.5 | 0.125 | |
| Strep. mitis L 796 | 0.125 | 0.125 | 0.25 | 0.5 | 0.25 | |
| Neisseria gonorrhoeae ISM68/126 | 32 | 64 | 64 | 64 | >128 | |
| Haemophilus influenzae ATCC 19418 | 64 | 64 | 128 | >128 | >128 | |
| Escherichia coli SKF 12140 | 8 | 32 | 8 | >128 | >128 | >128 |
| Proteus vulgaris ATCC 881 | 128 | >128 | 64 | >128 | >128 | >128 |
| Pseudomonas aeruginosa ATCC 10145 | 64 | >128 | 64 | >128 | >128 | >128 |

| | Compound No. | | | | | | |
|---|---|---|---|---|---|---|---|
| | 19 | 20 | 21 | 22 | 23 | 24 | 25 |
| Staph. aureus Tour L 165 | 1 | 0.5 | 2 | 0.06 | 0.5 | 0.25 | 0.25 |
| Staph. haemolyticus L 602 | 4 | 4 | 4 | 0.5 | 8 | 0.25 | 0.25 |
| Staph. epidermidis ATCC 12228 | 0.5 | 0.25 | 1 | | 0.25 | 0.125 | 0.125 |
| Strep. pyogenes C 203 | 0.25 | 0.125 | 0.125 | 0.125 | 2 | 0.125 | 0.125 |
| Strep. pneumoniae UC41 | 0.5 | 0.25 | 0.25 | | 0.5 | 0.25 | 0.125 |
| Strep. faecalis ATCC 7080 | 4 | 0.5 | 2 | | 1 | 0.5 | 1 |
| Strep. mitis L 796 | 0.25 | 0.125 | 0.25 | | 2 | 0.125 | 0.125 |
| Neisseria gonorrhoeae ISM68/126 | >128 | >128 | >128 | | >128 | 128 | >128 |
| Haemophilus influenzae ATCC 19418 | >128 | >128 | >128 | | >128 | >128 | >128 |
| Escherichia coli SKF 12140 | >128 | >128 | >128 | 32 | >128 | 32 | 32 |
| Proteus vulgaris ATCC 881 | >128 | >128 | >128 | | >128 | 128 | 64 |
| Pseudomonas aeruginosa ATCC 10145 | >128 | >128 | >128 | | >128 | >128 | >128 |

In view of the above reported antimicrobial activity, the compounds of the present invention can effectively be employed as the active ingredient of antimicrobial preparations used in human and veterinary medicine for the prevention and treatment of infectious diseases caused by pathocenic bacteria which are susceptible to said active ingrediants.

In such treatments, these compounds may be employed as such or in the form of mixtures in any proportion. The compounds of the present invention can be administered orally, topically or parenterally wherein however, the parenteral administration is preferred. Depending on the route of administration, these compounds can be formulated into various dosage forms. Preparations for oral administration may be in the form of capsules, tablets, liquid solutions or suspensions. As known in the art the capsules and tablets may contain in addition to the active ingredient, conventional excipients such as diluents, e.g. lactose, calcium phosphate, sorbitol and the like, lubricants, e.g. magnesium stearate, talc, polyethylene glycol, binding agents, e.g. polyvinylpyrrolidine, gelatin, sorbitol, tragacanth, acacia, flavoring agents, and acceptable disintegrating and wetting agents. The liquid preparations generally in the form of aqueous or oily solutions or suspensions, may contain conventional additives such as suspending agents.

For topical use the compounds of the present invention may also be prepared in suitable forms for absorption through the mucous membranes of the nose and throat or bronchial tissues and may conveniently take the form of liquid sprays or inhalants, lozenges, or throat paints.

For medication of the eyes or ears, the preparation may be presented in liquid or semi-liquid form. Topical applications may be formulated in hydrophobic or hydrophilic bases as ointments, creams, lotions, paints, or powders.

For rectal administration the compounds of the invention are administered in the form of suppositories admixed with conventional vehicles, such as, for example, cocoa butter, wax, spermaceti or polyethylenglycols and their derivatives.

Compositions for injection may take such forms as suspension, solutions, or emulsions in oily aqueous vehicles, and may contain formulatory agents such as suspending, stabilizing and/or dispersing agents. Alternatively, the active ingredient may be in powder form for reconstitution at the time of delivery with a suitable vehicle, such as sterile water.

The amount of active principle to be administered depends on various factors such as the size and conditions of the subject to be treated, the route and frequency of administration, and the causative agent involved. The compound of the invention are generally effective at a dosage comprised between about 0.5 and about 30 mg of active ingredient per Kg of body weight, preferably divided in 2 to 4 administrations per day. Particularly desirable compositions are those prepared in the form of dosage units containing from about 20 to about 300 mg per unit.

Representative examples of preparation of pharmaceutical compositions are as follows:

A parenteral solution is prepared with 100 mg of compound No 3 dissolved in 2 ml of sterile water for injection. A parenteral solution is prepared with 250 mg of compound N 19 hydrochloride dissolved in 3 ml of sterile water for injection. A topical ointment is prepared with 200 mg of compound No 19.
3.6 g of polyethylene glycol 4000 U.S.P.
6.2 g of polyethylene glycol 400 U.S.P.

Besides their activity as medicaments, the compounds of the present invention can be used as animal growth promoters. For this purpose, one or more of the compounds of the invention is administered orally in a suitable feed. The extract concentration employed is that which is required to provide for the active agent in a growth promotant effective amount when normal amounts of feed are consumed. The addition of the active compounds of the invention to animal feed is preferably accomplished by preparing an appropriate feed premix containing the active compounds in an effective amount and incorporating the premix into the complete ration.

Alternatively, an intermediate concentrate or feed supplement containing the active ingredient can be blended into the feed. The way in which such feed permixes and complete rations can be prepared and administered are described in reference books (such as "Applied Animal Nutrition", W. H. Freedman and Co., S. Francisco, USA, 1969 or "Livestock Feeds and Feeding", O and B Books, Corvallis, Oreg., USA, 1977).

The potentiometric determinations reported in the examples are run in Methylcellosolve:water, 4:1 (v/v). An excess of 0.01N HCl In this solvent mixture was added to the sample and the resulting solution was titrated with 0.01N NaOH in the same solvent mixture. The pK value obtained under the conditions is reported below as $pK_{MCS}$, wherein MCS stands for Methylcellosolve.

The following preparations and examples further illustrate the invention

PREPARATION 1 a) Preparation of $N^{15}$-tert-butyloxycarbonyl deglucoteicoplanin (intermediate III)

To a stirred solution of 45 g (about 37 mmol) of antibiotic L 17392 (deglucoteicoplanin) in 600 ml of DMF, 19.3 g (about 65 mmol) of tert-butyl-2,4,5-trichlorophenylcarbonate and 10.2 ml (about 74 mmol) of TEA are added. The reaction mixture is stirred at room temperature for 24 h afterwards it is pured into 1.5 L of water. The resulting solution is adjusted to pH 3 with 1N hydrochloric acid, then it is extracted with 3 L of a mixture ethyl acetate:n-butanol 2:1 (v/v). The organic layer is separated, washed with 1 L of water, then it is concentrated at 40° C. under vacuum to a volume of about 300 ml. On adding 700 ml of ethyl ether, a solid separates which is collected by filtration, washed with 200 ml of ethyl ether and dried at room temperature in vacuo overnight, yielding 44 g (92%) of pure title compound.

Preparation of $N^{15}$-carbobenzyloxy-deglucoteicoplanin (intermediate IV)

A solution of 4.5 ml of benzylchloroformate in 10 ml of dry acetone is added dropwise at room temperature to a stirred solution of 30 g (about 25 mmoles) of antibiotic L 17392 (deglucoteicoplanin) and of 6 ml (about 44 mmoles) of TEA in 300 ml of DMF. After about 120 min, 600 ml of ethyl ether is added and the precipitate (37 g) is collected by filtration and redissolved in 1.5 l of a mixture Acetone/Water 1:1 (v/v). The resulting solution is concentrated at 35° C. in vacuo to a small volume of about 0.7 l, then it is extracted with 1 l of ethyl ether which is separated and discarted. The aqueous layer is adjusted to pH 2–3 with 1N HCl and extracted with a mixture of n-butanol (0.7 L) and ethyl acetate (0.3 l). The organic layer is separated, washed with water (2×500 ml), then it is concentrated to a volume of about 200 ml in vacuo at 45° C. Adding ethyl ether (800 ml) a solid separates which is collected by filtration, washed with ether (150 ml) and dried overnight in vacuo at room temperature, yielding 31.3 g (about 94%) of pure title compound.

c) Preparation of $N^{15}$-CBz antibiotic L 17054

A solution of 0.45 ml of benzyl chloroformate in 10 ml of dry acetone is added dropwise, while cooling at 0°–3° C., to a stirred solution antibiotic L 17054 (3.2 g, 2 mmoles) and 0.5 g of $NaHCO_3$ in 150 ml of a mixture acetone:water, 2:1 (v/v). After about 30 min, 500 ml of water is added and the resulting solution is extracted with 500 ml of ethyl ether. The aqueous layer is adjusted to about pH 3.5 with 1N HCl and then is extracted with 500 ml of n-butanol. The organic layer is separated, washed with 400 ml of water (2×200 ml), then concentrated to a small volume at 45° C. under vacuum. On adding ethyl ether a solid separates which is collected, washed with ether and dried at room temperature in vacuo overnight, yielding 2.7 g of the compound of the title having a purity (HPLC titre>90%), enough for the next step.

d) Preparation of $N^{15}$-CBz-deglucoteicoplanin methyl ester (intermediate V)

To a solution of $N^{15}$-CBz-deglucoteicoplanin (see above under b) (55 g, 41.3 mmoles) in 1.1 l of DMF, KHCO$_3$ (4.4 g, 44.0 mmoles) is added under stirring. When the dissolution is complete the mixture is cooled to 5°–10° C. and 2.8 ml of methyl iodide are added dropwise. The reaction is stirred at room temperature overnight, the pH is corrected to 5, then the mixture is concentrated in vacuo at 50° C. to 250 ml and diluted with 2 l of water. The pH is adjusted to 2 with 1N HCl and the suspension extracted with 2 l of a mixture ethyl acetate/n-Butanol 2:1. The organic layer is washed with water (2×100 ml) and concentrated in vacuo, then the residue is treated with Ethyl ether and the precipitate filtered, washed with ether and dried, yielding 49 g of crude material that is purified on 1.5 Kg of silanized Silica-gel, eluting with a gradient from 25% to 50% of CH$_3$CN in water. The product is recovered with the 40% of CH$_3$CN, yielding 35 g of pure title compound.

e) Preparation of $N^{15}$-t-Boc-deglucoteicoplanin methyl ester (intermediate VI)

Starting from $N^{15}$-t-Boc-deglucoteicoplanin (see above under a) and using substantially the procedure described above under d) the title compound was obtained.

f) Preparation of $N^{15}$-t-Boc-deglucoteicoplanin cyanomethyl ester (intermediate VII)

A solution of 44 g (about 33 mmol) of $N^{15}$-t-BOC deglucoteicoplanin, 4.7 ml (about 34 mmol) of TEA and 44 ml of chloroacetonitrile in 440 ml of DMF is stirred at room temperature for 20 h, afterwards 1 l of ethyl acetate is added and the precipitate is collected by filtration. It is re-dissolved (about 46 g) in 1.5 l of a mixture methanol:water 1:2 (v/v) and the resulting solution is adjusted to pH 5.6 with glacial acetic acid. After adding 2 l of n-butanol, the most methanol is evaporated at 30° C. under vacuum and the organic layer is separated, washed with 1 l of water, then it is concentrated at 35° C. under vacuum to a final volume of about 300 ml. On adding 700 ml of ethyl ether, a solid separates which is collected by filtration, washed with 500 ml of ethyl ether, then it is dried at room temperature in vacuo overnight to give 42.5 g (96%) of pure title compound.

g) Preparation of $N^{15}$-t-Boc-deglucoteicoplanin methyl amide (intermediate VIII)

N-t.Boc-deglucoteicoplanin cyanomethyl ester (intermediate VII; 2 g) is reacted at room temperature with 150 ml of 25% ethanolic methylamine for 2 h to give 1.4 g of the compound of the title after recovery by concentration to dryness of the pooled fractions titre>90% eluted from a reverse phase silica gel chromatography eluted with a gradient from 20% to 50% of acetonitrile in water.

h) Preparation of $N^{15}$-CBz antibiotic L 17054 methyl ester (intermediate IX)

To a solution of $N^{15}$-CBz antibiotic L 17054 (see above 5 under c) (500 mg, 0.3 mmoles) in 5 ml of DMSO, KHCO$_3$ (50 mg, 0.5 mmoles) is added and the suspension is heated to 40° C. for 15 minutes. Afterwards the solution is cooled to 5° C. and methyl iodide (50 microl) is added; after one night at room temperature the reaction is worked up as above (see under e) yielding 450 mg of the title compound.

i) Preparation of $N^{15}$-t-Boc-deglucoteicoplanin 2-bromoethyl ester (intermediate X);

To a solution of $N^{15}$-t-Boc-deglucoteicoplanin (5 g, 3.87 mmoles) in 50 ml of DMSO, KHCO$_3$ (500 mg, 5 mmoles) and 1,2-dibromoethane (5 ml, 58 mmoles) is added under stirring at room temperature. After 120 minutes the reaction mixture is poured into water (500 ml), the pH is adjusted to 5 and the precipitate is filtered, washed with water and collected as a crude material which is then purified on a reverse-phase chromatographic column eluting with a gradient from 10% to 50% of acetonitrile in water at about pH 3 (hydrochloric acid) obtaining 485 g of the title compound.

l) Preparation of $N^{15}$-t-Boc-deglucoteicoplanin phenylmethyl ester (intermediate XI)

This compound is prepared as described above for the intermediate X (c.f. point i) using benzyl bromide (5 ml, 20 mmoles) instead of 1,2-dibromoethane obtaining 5.04 g of the desired product.

EXAMPLE 1

Preparation of $O^{56}$-(2,3-epoxypropyl)deglucoteicoplanin methyl ester (compound 1)

To a solution of intermediate V (see preparation 1 d), (2,5 g, 1.8 mmoles) in 50 m of DMSO, K$_2$CO$_3$ (250 mg, 1.8 mmoles) is added and the mixture is heated at 40° C. for 15 min. Afterwards 1-bromo-2,3-epoxypropane (about 2 mmoles) is added and the mixture is heated at 40° C. for 15 min. Afterwards, 1-Bromo-2,3-epoxypropane (about 2 mmoles) is added and the mixture is stirred at room temperature overnight. The reaction mixture is diluted with 300 ml of water, adjusted to pH 4–5 with 1N HCl and extracted with ethyl acetate/n-Butanol 8:2 (2×150 ml). The organic layer is washed with water (2×50 ml), dried over Na$_2$SO$_4$ and the solvents are removed in vacuo. The residue, treated with ethyl ether, is collected by filtration and dried in vacuo, yielding 2.7 g of crude intermediate XIII. This material is purified by reverse-phase column chromatography as described above (see Preparation 1 i) yielding 1.9 g of pure intermediate XIII. This material is dissolved in methanol (100 ml) containing 2 ml of 1N HCl, then it is hydrogenated (1 atm., 20° C.) in the presence of 1 g of 10% Pd/BaSO$_4$ for 4 h. After separation of the catalyst, the solvent is removed from the filtrate at 30° C. in vacuo and the residue is treated with ethyl ether and collected by filtration, yielding 1.7 g of pure title compound as the hydrochloride.

EXAMPLE 2

Preparation of $O^{56}$-[4(N-phthalimido)butyl]deglucoteicoplanin methyl ester (compound 2)

To a solution of intermediate V (2 g, 1.48 mmoles) in 80 ml of DMF containing K$_2$CO$_3$ (414 mg, 3 mmoles) and molecular sieves 4A (3 g), N-(4-Bromobutyl) phthalimide (420 mg, 1.48 mmoles) is added and the mixture is stirred at room temperature for 6 h. Afterwards a second portion of bromobutyl phthalimide (420 mg) is added and the reaction is allowed to stand overnight. The mixture is diluted with 400 ml of water and the suspension, adjusted to pH 4 with 1N HCl, is extracted with 200 ml of ethyl acetate/n-Butanol 8:2 (v/v). The organic layer is concentrated in vacuo and the residue is purified on a silica gel column (130 g) eluting with a mixture of $CH_2Cl_2$:MeOH, 9:1 (v/v) yielding 1 g (50%) of pure intermediate XIV. This product is dissolved in 80 ml of MeOH containing 1 ml of 1N HCl and hydrogenated with 10% Pd/$BaSO_4$ (400 mg) at 1 atm and room temperature. The catalyst is filtered on filter aid (Celite), the solvent is removed in vacuo from the filtrate and the solid is treated with ethyl ether, collected by filtration and dried, yielding 860 mg of pure title compound as the hydrochloride.

EXAMPLE 3

Preparation of $O^{56}$-(1-carboxy-3-hydroxypropyl)deglucoteicoplanin methyl ester hydrochloride (Compound 3)

Reacting intermediate V (2 g, 1.48 mmoles) with alpha-bromo-gamma-butyrolactone (250 microl, 3 mmoles), using substantially the procedure above mentioned for compound 2, the crude lactone (intermediate XII, 1.8 g) is obtained (The HPLC profile showed two peaks around 20% and 80% respectively, the first one having the lactone ring opened). This mixture is hydrogenated in order to remove the CBz protecting group as above reported and the solid obtained is purified by reverse-phase chromatography using a gradient from 15% to 40% of acetonitrile in 0.01N HCl, yielding 500 mg ( about 25%) of pure title compound as the hydrochloride. The IR spectra of this compound did not show any absorption that can be due to the lactone structure but showed only the methyl ester band at 1730 $cm^{-1}$; also NMR assignments and FAB measurements are consistent with title structure. Potentiometric titration gives two values: $pK_{mcs}$ 6 and 7.2.

EXAMPLE 4

Preparation of $O^{56}$-[1-[[2-aminoethylamino]carbonyl]3-hydroxypropyl]deglucoteicoplanin methyl ester hydrochloride (Compound 4)

Intermediate XII (see above) (1.2 g, 8.3 mmoles) is dissolved in a mixture of absolute ethanol (100 ml) and acetonitrile (20 ml). 1,2-Ethylenediamine (1 ml) is added and the mixture is stirred overnight at room temperature. The resulting suspension is concentrated at 40° C. in vacuo, then ethyl ether (100 ml) is added, the solid is collected by filtration, washed with ether and dried in vacuo yielding 1.4 g of crude $N^{15}$-CBz-derivative of compound of the title (intermediate XV). This compound is purified on a silica gel column (150 g) eluting with $CHCl_3$/MeOH 95:5 (v/v). The material recovered (240 mg), dissolved in 25 ml of MeOH containing 1 ml of 1N HCl, is hydrogenated with 10% Pd/C (200 mg) at 1 atm and room temperature for 5 h. The catalyst is filtered on a filter aid "Celite", the solvent is removed in vacuo from the filtrate and the solid residue is treated with ethyl ether, filtered and dried in vacuo, yielding 220 mg of the title compound. Potentiometric titration:$pK_{MCS}$ 5.75 and 6.75.

EXAMPLE 5

Preparation of $O^{56}$-(4-aminobutyl)deglucoteicoplanin methyl ester (Compound 5)

Compound 2 (1 g, 0.7 mmoles) is dissolved in a mixture of absolute ethanol (80 ml) and acetonitrile (20 ml), then 0.5 ml of $NH_2NH_2.H_2O$ is added and the reaction is stirred overnight at room temperature. The solvents are removed in vacuo and the obtained crude material is purified on a silanized Silica-gel column (60 g) eluting the side products first with a gradient from 35% to 45% of acetonitrile in water (600 ml), then the desired product with 300 ml of MeOH containing 1% N HCl The fractions containing the pure compound of this title (>95% HPLC titer) are pooled and the solvent is removed to dryness, yielding 320 mg of title compound as the hydrochloride.

EXAMPLE 6

Preparation of $O^{56}$-[4-[bis[2-(dimethyl amino)ethyl]amino]butyl]deglucoteicoplanin methyl ester (Compound 6)

Intermediate XIV is treated with hydrazine monohydrate as reported for preparation of compound 5 obtaining intermediate XVI. To a solution of this compound (600 mg, 0.42 mmoles) in acetonitrile (10 ml) and MeOH (3 ml), N,N-Dimethylacetaldehyde hydrochloride ( 100 mg, 0.81 mmoles) is added. The mixture is stirred for 10 minutes, then $NaCNBH_3$ (50 mg) is added. The reaction is stirred at room temperature for two hours then the two reagents are added again twice by one hour interval. The reaction mixture is stirred overnight at room temperature, then it is diluted with MeOH (20 ml) and adjusted to pH 2 with 1N HCl. The solvents are removed in vacuo and the solid, treated with water (30 ml), is centrifuged. The liquid phase is discarded and the solid (intermediate XXI) is dissolved in 80 ml of a mixture MeOH/$CH_3CN$ 1:1 (v/v) and 1 ml 1N HCl. This solution is hydrogenated for 12 h and worked up as above reported, yielding 500 mg of crude title compound. This solid is dissolved in 0.1N HCl (50 ml) and extracted with a mixture of ethyl acetate/n-Butanol, 70:30 (50 ml). The organic layer is discarded while the aqueous solution is adjusted to pH 8 with 1N NaOH, the solid which forms is collected by filtration, washed with a few drops of water and dried in vacuo overnight at 45° C., yielding 150 mg of the title compound.

EXAMPLE 7

Preparation of $O^{56}$-(2-chloroethyl) deglucoteicoplanin methyl ester (Compound 7)

To a stirred solution of intermediate VI (10 g 7.6 mmoles) in 200 ml of DMF, powdered dry $K_2CO_3$ (1.5 g, 10.8 mmoles) is added and the suspension heated to 40° C. After 15 minutes 2-chloroethyl-p-toluenesulfonate (2 ml, 11 mmoles) is added and the mixture is kept at 40° C. for 4 h. The solution is cooled to 10° C. and it is poured into 1.5 l of water and the pH is adjusted to 4–5 with 1N HCl. The resulting suspension is centrifuged, the mother liquor is discarded and the solid is dissolved with n-Butanol/ethyl acetete 1:1 (500 ml) and washed with 150 ml of water. The organic layer is concentrated in vacuo and the residue, diluted with 500 ml of ethyl ether, forms a precipitate which is collected, washed with ether and dried, yielding 12.5 g of a crude material that is purified on a silica gel column eluting with a mixture of $CH_2Cl_2$/MeOH 87.5/12.5 (v/v) yielding 5.2 g of the pure $N^{15}$-Boc derivative of the title compound, with FAB M+ =1374, NMR and microanalysis confirming its structure (intermediate XX). This compound (500 mg) is suspended in $CH_2Cl_2$ (2 ml) and carefully treated with 1.5 ml of $CF_3COOH$ at room temperature for 15 minutes. The solvents are removed in vacuo and the residue is purified on silanized Silica-gel column eluting with 30% acetonitrile in water thus obtaining 220 mg of pure title compound.

EXAMPLE 8

Preparation of $O^{56}$-(2-hydroxyethyl) deglucoteicoplanin methyl ester (Compound 8)

The reaction between intermediate VI (2 g, 1.52 mmoles) and 2-bromoethanol (600 microl, about 7 mmoles) substantially following the procedure of Example 2, obtaining the $N^{15}$Boc derivative of the compound of the title (1.54 g). This compound shows a $t_R$ in reverse-phase HPLC only 0.3 minutes less than VI. The protecting group is removed with $CF_3COOH$ as previously described, afterwards the material is purified on a silanized Silica-gel column eluting with 15% of acetonitrile in water, yielding 150 mg of pure title compound.

EXAMPLE 9

Preparation of $O^{56}$-(4-aminobutyl)-deglucoteicoplanin methylamide (Compound 9)

Intermediate VIII (2 g, 1.5 mmoles) is treated with N-(4-bromobutyl)phthalimide substantially following the procedure reported in Example 2 for the preparation of intermediate XIV yielding 2 g of intermediate XVIII. This compound is reacted with Hydrazine monohydrate in order to open the phthalimidoyl protective group as previously reported (Example 5), yielding 2.2 g of crude $N^{15}$Boc title compound (intermediate XIX). This material is purified by semi-preparative reverse-phase low pressure chromatography, on ICN SILICA RP-8 (32–63 um) 60 A packed in a glass column, using a gradient from 15% to 35% of Acetonitrile in 0.01N HCl. The yield is 1 g of semi pure XIX. The $N^{15}$-protective group is removed with $CF_3COOH$ as previously reported and the final product is purified on a silanized Silica gel column yielding 350 mg of pure title compound.

EXAMPLE 10

Preparation of $O^{56}$-(4-aminobutyl)teicoplanin pseudoaglycone methyl ester (Compound 10)

To a stirred solution of intermediate IX (1.4 g, 0.8 mmoles) (Preparation 1 h) in 30 ml of DMSO, $K_2CO_3$ (250 mg, 1.8 mmoles) is added and the mixture is heated at 40° C. for 15 minutes, then N-(4-bromobutyl)phthalimide (100 mg, 0.35 mmoles) is added. The reaction is carried out following substantially the procedure of Example 2, yielding 900 mg of intermediate XXII after chromatography on silanized Silica-gel using an isocratic system of acetonitrile (38%) in water. Compound XXII, treated with hydrazine monohydrate (300 ul, 6.3 mmoles) as previously described (c.f. Example 5), yields 800 mg of intermediate XXIII which is dissolved in 100 ml EtOH/water/AcOH, 7:2:1 and hydrogenated for about 3 h on 700 mg of 5% Pd/C in order to remove the CBz-protective group. The solution is worked up as usual, yielding 600 mg of the title compound.

EXAMPLE 11

Preparation of $O^{56}$-(2-bromoethyl)deglucoteicoplanin methyl ester (Compound 11)

Intermediate V (6 g, 4.4 mmoles) is dissolved in DMSO (60 ml) and potassium carbonate (620 mg, 4.5 mmoles) is added while stirring the mixture at 40° C. for 15 minutes; afterwards 1.5 ml, 17 mmoles) of 1,2-dibromoethane is added. The mixture is stirred for 4 h at 40° C. and overnight at room temperature. Then it is diluted with 400 ml of water, the pH is adjusted to 5 with 1N HCl and the resulting suspension is centrifuged. The solid is recovered by filtration, washed with water and dried in vacuo at 40° C. overnight, yielding 6 g of crude intermediate XXV. This material is purified on a Silica-gel column packed in $CH_2Cl_2$ eluting with increasing percentages of MeOH/AcOH in methylene chloride. The compound is eluted with the mixture $CH_2Cl_2$/MeOH/AcOH 94:6:2 yielding 2 g of pure intermediate XXV, 150 mg of which is dissolved in a mixture of MeOH (15 ml) and N/10 HCl (5 ml) and hydrogenated for 4 h (1 atm, room temperature) on 75 mg of 5% Pd/C. The mixture is worked up as usual, (c.f. Example 4) yielding 120 mg of the title compound.

EXAMPLE 12

Preparation of $O^{56}$-(cyanomethyl)deglucoteicoplanin cyanomethyl ester trifluoroacetate salt (Compound 12)

To a solution of 15-N-Boc-deglucoteicoplanin (intermediate III) (11 g, 8.46 mmoles) in 60 ml of DMF, potassium bicarbonate (1.5 g, 15 mmoles) is added and the mixture is heated to 40° C. for 15 minutes, then chloroacetonitrile (10 ml, 15.8 mmoles) is added dropwise during 20 minutes and the mixture is allowed to stir at 40° for 5 h. The reaction mixture is cooled and ethyl ether (300 ml) is added, the solid material which forms is recovered by filtration, dissolved in ethyl acetate (200 ml) and washed with acidic water. The organic solvent is removed in vacuo and the residue is purified on a Silica-gel column packed in Methylene chloride eluting with a mixture $CH_2Cl_2$/MeOH/AcOH 90:10:2 (v/v), yielding 6 g of 15-N-Boc-derivative of the compound of the title (intermediate XXIV), 250 mg of which is hydrolyzed with anhydrous Trifluoroacetic acid as previously reported (see Example 7) yielding 200 mg of the title compound.

EXAMPLE 13

Preparation of $O^{56}$-[2-(1-pyrrolidinyl)ethyl]deglucoteicoplanin methyl ester dihydrochloride (Compound 13)

Pyrrolidine (700 microl, 8.38 mmoles) is added to a stirred solution of intermediate XXV (Example 11,) (700 mg, 0.5 mmoles) in absolute EtOH (40 ml) and DMSO (20 ml), afterwards the reaction is heated to 50° for 8 h. The mixture is diluted with 300 ml of chilled water and the solid recovered by centrifugation. This material is dissolved in 40 ml of 30% THF in water at pH 6.5 (N HCl) and loaded on a silanized Silica-gel column, then it is eluted using an isocratic sistem of 30% Acetonitrile in water. Fractions are worked up as usual, yielding 400 mg of pure intermediate XXVI (N-CBz derivative of the compound of the title). This material (350 mg), dissolved in MeOH (45 ml) and N/10 HCl (15 ml) is hydrogenated on 200 mg of 5% Pd/C for 3 h. The mixture is worked up, as usual, yielding 280 mg of the title compound (HPLC purity 85%). Potentiometric titration: $pK_{MCS}$6.4; 7.2. FAB M+1310.

EXAMPLE 14

Preparation of $O^{56}$-[2-(1-morpholinyl)ethyl]deglucoteicoplanin methyl ester dihydrochloride (Compound 14)

Following the procedure above reported for the preparation of compound 13 but replacing pyrrolidine with morpholine, intermediate XXVII (800 mg) is obtained starting from 900 mg of intermediate XXV. This compound is deprotected by hydrogenation on 400 mg of 5% Pd/C producing 600 mg of an 80/20 mixture of title compound and its 22-dechloro-derivative (80/20). This material is purified on a silanized Silica-gel column eluting with 15% acetonitrile in 0.01N HCl, yielding 150 mg of pure title compound. Potentiometric titration: $pK_{MCS}$ 5.2; 7.1.

EXAMPLE 15

Preparation of
$O^{56}$-[2-(1-ethylendiaminyl)ethyl]deglucoteicoplanin ethylenediamine amide (Compound 15)

Starting from intermediate VII and following the procedure described in Preparation 10, substituting methyl amine with ethylendiamine, $N^{15}$-BOC-deglucoteicoplanin ethylenediamine amide was obtained. This compound (3.5 g, 2.6 mmoles) was protected at the primary amino group of the amide moiety with BOC by reaction with 1-butyl 2,4,5-trichlorophenyl carbonate in DMF (30 ml) and in presence of TEA (0.6 ml) according to the known procedure; after silanized Silica-gel column purification, intermediate XXVIII (2 g) is obtained in pure form (Fab M+1440.39, low isotopic contribution). This compound reacts with 1,2-dibromo ethane (425 ul) in DMSO (17 ml) in the presence of potassium carbonate (175 mg). After one night at room temperature, a second portion of 1,2-dibromoethane (450 microl) and $K_2CO_3$ (200 mg) is added and the reaction is allowed to stir for 12 h. The mixture is then diluted with chilled water (300 ml), the pH adjusted to 5 and the product recovered by centrifugation. This material is dissolved in 200 ml of ethyl acetate, the mixture is washed with water and the solvent is removed in vacuo. The obtained residue is dissolved in n-butanol and the mixture is concentrated in vacuo to a final volume of 5 ml; then ethyl ether is added (400 ml) and the solid is recovered by filtration, yielding 1.5 g of intermediate XXIX. This intermediate is treated substantially as described in Example 13 for intermediate XXV but substituting pyrrolidine with ethylenediamine (1.5 ml). The crude material obtained is purified on a silanized Silica-gel column eluting with a mixture of 30% Acetonitrile in water with a pH gradient starting from 0 to 1.5% of IN HCl, yielding 650 mg of pure intermediate XXX. Intermediate XXX (620 mg) is treated with trifluoroacetic acid in $CH_2Cl_2$ for 20 minutes to remove the two BOC protective groups. The solvents are then removed in vacuo and the residue is taken up with ethyl ether, collected by filtration, washed with ether and dried in vacuo overnight, yielding 500 mg of pure title compound. This compound is not detectable by HPLC with the above reported analytical conditions: it is detected by TLC with RP-8 layer ( Merck) eluting with 35% acetonitrile in 5% aqueous $Na_2SO_4$; Rf 0.62, intermediate XXX $R_f$=0.25.

EXAMPLE 16

Preparation of
$O^{56}$-(tetrahydro-2-oxo-3-furanyl)deglucoteicoplanin (Compound 16)

A solution of 100 mg of compound 21 (see Example 21 for its preparation) (0.078 mmoles) in 10 ml of $MeOH/H_2O$, 7/3 adjusted to pH 3 with HCl is hydrogenated under room pressure and temperature in the presence of 50 mg of 5% Pd/C for 2 h under vigorous stirring. Then the pH is adjusted to about 6 and the methanol is removed under reduced pressure, the resulting suspension is centrifuged and the solid collected by filtration is washed with water and dried giving 55 mg of pure title compound.

EXAMPLE 17

Preparation of $O^{56}$-(2-bromoethyl)deglucoteicoplanin 2-bromoethyl ester hydrochloride salt (Compound 17)

To a solution of intermediate X (5 g, 3.56 mmoles) in 50 ml of DMSO, $K_2CO_3$ (550 mg, 4 mmoles) and 1,2-dibromoethane (5 ml, 58 mmoles) are added under stirring and the solution is heated at 50° C. for 2 h. Then, after cooling, it is poured into 300 ml of water, the pH is adjusted to about 6 and the precipitate is filtered, washed with water and dried obtaining 5.47 g of intermediate XXXI. This compound (1 g, 0.66 mmoles) is dissolved into 2 ml of trifluoroacetic acid and stirred for 5 minutes, then it is concentrated under reduced pressure "in vacuo" at room temperature and treated with ethyl ether. The resulting solid is collected by filtration, washed with ethyl ether and dried to obtain 1.02 g of the crude title compound which is purified by reverse-phase cromatography eluting with a gradient from 20 to 60% of acetonitrile in water, adjusted to pH 3 with HCl; the pure fractions collected yield 0.76 g of pure title compound, upon working up as usual.

EXAMPLE 18

Preparation of
$O^{56}$-[2-[2-[(2-methoxy-2-oxoethyl)amino]-2-oxoethyl amino]ethyl]deglucoteicoplanin 2-bromoethyl ester (Compound 18)

To a solution of intermediate XXXI (1 g, 0.66 mmoles) in 10 ml of DMSO, $K_2CO_3$ (220 mg, 1.6 mmoles) and glycyl glycine methyl ester hydrochloride (260 mg, 1 mmole) are added under stirring and the solution is kept at 40° for 6 h. After cooling, the mixture is poured into 50 ml of water adjusting the pH to about 6, the precipitate is filtered, washed with water and dried obtaining 0.93 g of intermediate XXXII. This compound (0.90 g, 0.57 mmoles) is dissolved in 2 ml of trifluoroacetic acid and treated as in Example 17 obtaining 0.52 g of the pure title compound.

EXAMPLE 19

Preparation of $O^{56}$-(2-bromoethyl)deglucoteicoplanin phenylmethyl ester (Compound 19)

To a solution of intermediate XI (1 g, 0.72 mmoles) in 10 ml of DMSO, $K_2CO_3$ (110 mg, 0.8 mmoles) and 1,2-dibromoethane (1 ml, 11.6 mmoles) are added under stirring and the solution is heated at 50° C. for 2 h. After cooling, the mixture is worked up as in Preparation 18 obtaining 0.87 g of intermediate XXXV. This compound (0.80 g, 0.53 mmoles) is treated with trifluoroacetic acid as described above (see Example 17) yielding 0.59 mg of pure title compound.

EXAMPLE 20

Preparation of $O^{56}$-phenylmethyldeglucoteicoplanin phenylmethyl ester (Compound 20)

The procedure is similar to that of Example 19 using benzyl bromide (1 ml, 8.4 mmoles) instead of 1,2-dibromoethane, passing through intermediate XXXIII, which is treated with trifluoroacetic acid (see Example 17) yielding 0.62 g of pure title compound.

EXAMPLE 21

Preparation of
O$^{56}$-(tetrahydro-2-oxo-3-furanyl)deglucoteicoplanin
phenylmethyl ester (Compound 21)

To a solution of intermediate XI (2 g, 1.45 mmoles) in 20 ml of DMSO, K$_2$CO$_3$ (220 mg, 1.6 mmoles) and alpha-bromo-gamma-butyrolactone (2 ml, 24 mmoles) are added under stirring and the mixture is kept at 50° C. for 2 h. After a work-up similar to that described in Example 18, 2.07 g of intermediate XXXVI are obtained. This compound (2 g, 1.36 mmoles) is treated as in Example 17 for intermediate XXXI to give 1.66 g of pure title compound.

EXAMPLE 22

Preparation of O$^{56}$-(2-hydroxyethyl)deglucoteicoplanin 2-hydroxyethyl ester (Compound 22)

To a solution of intermediate XXXI (100 mg, 0.066 mmoles) in 2 ml of DMSO NaOH in pellets (20 mg, 0.5 mmoles) is added and the solution is heated at 40° C. for 1 h. The solution, after cooling, is poured into 20 ml of phosphate buffer pH 4.4, the precipitate which forms is collected by filtration, washed with water and dried under reduced pressure producing 75 mg of intermediate XXXIV. This compound is treated with trifluoroacetic acid and worked up as described in Example 17, yielding 48 mg of pure title compound.

EXAMPLE 23

Preparation of
O$^{56}$-(tetrahydro-2-oxo-3-furanyl)deglucoteicoplanin (tetrahydro-2-oxo-3-furanyl) ester (Compound 23)

To a solution of N$^{15}$-BOC-deglucoteicoplanin (intermediate III) (5 g, 3.87 mmoles) in 50 ml of DMSO, K$_2$CO$_3$ (1.1 g, 8 mmoles) and alpha-bromo-gamma-butyrolactone (10 ml, about 120 moles) are added under stirring and kept for 3 h at 40° C. Working as in Example 18, 5.76 g of intermediate XXXVII is obtained that is then treated as described in Example 17 for intermediate XXXI, to give 4.14 g of pure title compound.

EXAMPLE 24

Preparation of O-(1-(2-aminoethyl)amino)
carbonyl)-3-hydroxypropyl) teicoplanin aglycone
1-(2-aminoethyl)amino)carbonyl)-3-hydroxypropyl
ester (Compound 24)

To a solution of compound 23 (1 g, 0.731 mmoles) in 10 ml of DMSO ethylenediamine is added (250 microl, 3.74 mmoles) under stirring at room temperature. After an hour the reaction mixture is treated as described in Example 18 obtaining 0.86 g of pure title compound.

EXAMPLE 25

Preparation of
O-(2-(3-(4-(3-amino-propyl)amino)butyl)amino)propyl-)amino)-1-hydroxy-2-oxoethyl)teicoplanin aglycone
1-(3-(4-(3-aminopropyl)
amino)butyl)amino)propyl)amino)carbonyl)-3-
hydroxy-propyl ester (Compound 25)

The reaction is carried out as in Example 24 but using spermine (1 g, 4.94 mmoles) instead of ethylenediamine and obtaining 0.74 g of pure title compound.

EXAMPLE 26

Preparation of O$^{56}$-(2-ethoxyethyl) deglucoteicoplanin (Compound 26)

To a solution of intermediates IV (500 mg, 0.38 mmoles) in 5 ml of DMSO, 1,8-diazabicyclo-(5,4,0) undec-7-ene (DBU, JANSSEN) (100 ml, 0.65 mmoles) and 2-chloroethyl ethyl ether (400 ml, 3.6 mmoles) are added under stirring and the mixture is kept at 40° C. for 48 h. After cooling, the mixture is poured into 50 ml of water the pH adjusted to 4 and extracted with n-butanol (80 ml×2).

The organic layer is washed twice with water (40 ml) and the solvent is removed in vacuo at 50° C. The residue, dried in vacuo overnight is hydrolyzed with anhydrous trifluoroacetic acid as reported (see Example 7) yielding 400 mg of crude material. This material is purified on a reversed-phase column as previously reported (see Example 9) using a gradient from 10% to 60% of acetonitrile. Fractions no. 20–26 (30 ml each) are pooled and worked up, yielding 80 mg of pure title compound.

We claim:
1. A teicoplanin derivative of formula I:

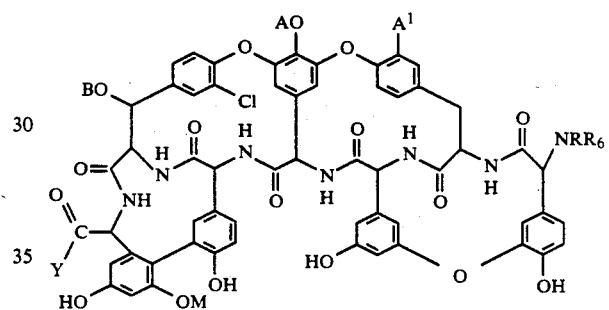

wherein
A represents (C$_1$-C$_6$)alkyl, (C$_5$-C$_6$)cycloalkyl, (C$_5$-C$_6$)cycloalkyl(C$_1$-C$_4$)alkyl, (C$_1$-C$_4$)alkoxy-(C$_1$-C$_4$)alkyl, hydroxy(C$_1$-C$_6$)alkyl, epoxy-(C$_3$-C$_6$)alkyl, 4–7 membered saturated or unsaturated cyclic lactone moieties selected from the group consisting of dihydrooxofuryl, tetrahydrooxofuryl, perhydrooxopyranyl, oxooxepyl and the tautomers thereof, halo(C$_1$-C$_6$)alkyl, cyano(C$_1$-C$_6$)alkyl, phenyl(C$_1$-C$_4$)alkyl wherein the phenyl ring is further substituted with substituent selected from chloro, bromo, iodo, (C$_1$-C$_3$)alkyl, (C$_1$-C$_3$)alkoxy, cyano, amino, and hydroxy; a group of formula (CH$_2$)$_2$ (CO)$_t$—R$^{13}$ wherein one of the hydrogen atoms of a CH$_2$ unit is replaced by a hydroxy-(C$_1$-C$_4$)alkyl group, s represents an integer from 1 to 6, t represents zero of 1, and R$^{13}$ represents hydroxy, (C$_1$-C$_4$) alkoxy or a 5–10 membered saturated, partially unsaturated or aromatic heterocyclic ring containing from 1 to 3 heteroatoms independently selected from nitrogen and oxygen, which are further optionally substituted on the ring carbons with 1 to 3 groups independently selected from oxo, chloro, bromo, and (C$_1$-C$_3$)alkyl, said ring selected from the group consisting of pyridinyl, pyrimidinyl, pyrazinyl, pyrrolidinyl, piperidinyl, piperazinyl, oxazolyl, oxazolinyl, oxazolidinyl, pyrazolinyl, pyrazolidinyl, thiazolidinyl, morpholinyl, thiomorpholinyl, pyrrolyl, pyrrolinyl, imidazolyl, imidazolidinyl, thiadiazolyl, oxadiazolyl, tetrazolyl, benzofuryl, benzopyranyl, benzopyrazolyl, purinyl, indazolyl, indolyl, 1,3-dihydro-1,3-dioxo-2H-isoindol-2-yl, isoindolyl, indolizinyl, quinolinyl, isoquinolinyl, quinozolinyl, and phtheridinyl; or a group of formula

[(CH$_2$)$_s$(CO)$_t$NR$^{14}$]$_u$R$^{15}$ wherein one of the hydrogen atoms of a CH$_2$ unit is replaced by a hydroxy(C$_1$-C$_4$)alkyl group, s and t are defined as above, u represents an integer from 1 to 6, R$^{14}$ represents a group selected from hydrogen, (C$_1$-C$_3$)alkyl, (CH$_2$)$_s$NH$_2$, (CH$_2$)$_s$NH (C$_1$-C$_2$)alkyl, and (CH$_2$)$_s$ N[(C$_1$-C$_2$)alkyl]$_2$, wherein s is defined as above, and R$^{15}$ represents hydrogen, (C$_1$-C$_4$)alkyl, (CH$_2$)$_s$ — COO(C$_1$-C$_4$)alkyl or (C$_5$-C$_6$)cycloalkyl;

A$^1$ represents chloro or hydrogen;

R represents hydrogen, (C$_1$-C$_2$)alkyl, (C$_4$-C$_7$)cycloalky, cyano (C$_1$-C$_3$)alkyl, —(CH$_2$)$_q$—OOC—(C$_1$-C$_6$)alkyl, wherein q is an integer selected from 1, 2, 3 and 4, substituted in the position ortho, meta and/or para with 1 to 3 groups selected from (C$_1$-C$_4$)alkyl, nitro, bromo, chloro, iodo, (C$_1$-C$_4$)alkoxy, and phenyl;

R$^6$ represents hydrogen, C$_1$-C$_{12}$)alkyl, (C$_4$-C$_7$)cycloalkyl, cyano (C$_1$-C$_3$)alkyl, —(CH$_2$)$_r$—OOC—(C$_1$-C$_6$)alkyl, wherein r is an integer selected from 1, 2, 3 and 4, or phenyl (C$_1$-C$_4$)alkyl wherein the phenyl group is optimally substituted in the position ortho, meta and/or para with 1 to 3 groups selected from (C$_1$-C$_4$)alkyl, nitro, bromo, chloro, iodo, (C$_1$-C$_4$)alkoxy, and phenyl; or R$^6$ represents a group [CHR$^7$ (CR$^9$ R$^9$)$_m$X]$_n$—R$^{10}$ wherein R$^7$ and R$^8$ independently represent H or a (C$_1$-C$_6$)alkyl;

R$^9$ represents H, a (C$_1$-C$_6$)alkyl or OH;

R$^{10}$ represents H, a (C$_1$-C$_3$)alkyl, COOR$^{11}$, OR$^{11}$, SR$^{11}$, NR$^{11}$R$^{12}$ or halogen;

R$^{11}$ and R$^{12}$ independently represent H or a (C$_1$-C$_3$)alkyl; m is zero or 1, n is an integer between zero and 6;

X is , NH or a bond with the proviso that when X is O or NH, then n is different from zero and R$^9$ is different from OH; with the proviso that when one between R and R$^6$ represents (CH$_2$)$_n$—OOC—(C$_1$-C$_6$)alkyl the other must represent hydrogen;

Y represents OR$^{16}$ wherein R$^{16}$ represents hydrogen, halo(C$_1$-C$_4$)alkyl, hydroxy(C$_1$-C$_4$)alkyl, (C$_1$-C$_4$)alkyl or phenyl(C$_1$-C$_4$)alkyl, wherein the phenyl ring is optionally substituted with 1 to 3 groups selected from (C$_1$-C$_3$)alkyl, (C$_1$-C$_3$)alkoxy, chloro, bromo and iodo; a group (CH$_2$)$_s$(CO)$_t$—R$^{13}$ or —[(CH$_2$)$_s$(CO)$_t$NR$^{14}$]$_u$R$^{15}$ wherein these groups are as defined above for the substituent A, or Y represents a group —NR$^1$R$^2$ wherein R$^1$ represents hydrogen, (C$_1$-C$_6$)alkyl, hydroxy-(C$_2$-C$_4$)alkyl, halogen(C$_2$-C$_4$)alkyl, (C$_1$-C$_4$)alkoxy-(C$_2$-C$_4$)alkyl, amino(C$_2$-C$_4$)alkyl, (C$_1$-C$_4$)alkylamino-(C$_2$-C$_4$)alkyl or di(C$_1$-C$_4$)alkylamino(C$_2$-C$_4$)alkyl;

R$^2$ represents hydrogen, (C$_1$-C$_6$)alkyl, hydroxy-(C$_2$-C$_4$)alkyl, halo(C$_2$-C$_4$)alkyl, (C$_1$-C$_4$)alkoxy(C$_2$-C$_4$)alkyl or a nitrogen containing 5-6 membered heterocyclic ring which is unsaturated, partially saturated or wholly saturated and optionally contains 1 to 3 further heteroatoms selected from N, S and O, said ring selected from the group consisting of pyridinyl, pyrimidinyl, pyrazinyl, pyrrolidinyl, piperidinyl, piperazinyl, oxazolyl, oxazolinyl, oxazolidinyl, pyrazolinyl, pyrazolidinyl, thiazolidinyl, morpholinyl, thiomorpholinyl, pyrrolyl, pyrrolinyl, imidazolyl, imidazolidinyl, thiadiazolyl, oxadiazolyl, tetrazolyl, 1-azabicyclo[2.2.2]octane, 1,4-diazabicyclo[3.2.2]nonane, 1-azabicyclo[2.2.1]heptane, 1-azabicyclo[3.2.1]octane, 8-azabicyclo[3.2.1]octane, 3-azabicyclo[3.2.1]octane, 1-azabicyclo[3.3.1]nonane, 9-azabicyclo[3.3.1]nonane, 3,8-diazabicyclo[3.2.1]octane, 2-azabicyclo[2.2.1]heptane, 2-azabicyclo[2.2.2]octane and 3-azabicyclo[3.2.2]nonane, wherein 1 to 3 of the ring carbons optionally bears (C$_1$-C$_4$)alkyl substituents and one of the nitrogen rings optionally bears a substituent R$^5$ selected from (C$_1$-C$_4$)alkyl, (C$_4$-C$_7$)cycloalkyl, phenyl optionally substituted with halogen or (C$_1$-C$_4$)alkyl, phenyl (C$_1$-C$_4$)alkyl, pyridyl and (C$_1$-C$_4$)alkylpyridinio, and when the ring is wholly saturated two of the ring members are optionally bridged by an alkylene chain of 1 to 3 carbon atoms wherein one of the methylene groups is optionally replaced by —NH— or —N[(C$_1$-C$_4$)alkyl]; a group —alk—W wherein "alk" represents a linear alkylene chain of 1 to 8 carbon atoms which is optionally substituted with a substituent selected from (C$_1$-C$_4$)alkyl, hydroxy (C$_1$-C$_4$)alkyl, hydroxy, carboxy aminocarbonyl, (C$_1$-C$_4$)alkylaminocarbonyl, di(C$_1$-C$_4$)alkylaminocarbonyl, (C$_1$-C$_4$)alkylcarbonyl, phenyl (C$_1$-C$_4$)alkoxycarbonyl, and (C$_1$-C$_4$) alkoxycarbonyl; and W represents a carboxy, (C$_1$-C$_4$)alkoxycarbonyl, and phenyl (C$_1$-C$_4$)alkoxycarbonyl, aminocarbonyl, (C$_1$-C$_4$)alkylaminocarbonyl, di(C$_1$-C$_4$)alkylaminocarbonyl, ureido, guanidino, a nitrogen containing 5-6 membered heterocyclic ring defined as above, a group of the formula —NR$^3$R$^4$ wherein R$^3$ and R$^4$ each independently represent hydrogen, (C$_1$-C$_6$)alkyl, hydroxy(C$_2$-C$_4$)alkyl or halo(C$_2$-C$_4$)alkyl or R$^4$ represents phenylmethyloxycarbonyl and R$^3$ represents hydrogen; or R$^1$ and R$^2$ taken together with the adjacent nitrogen atom represent a saturated 5-7 membered heterocyclic ring which optionally bears one to two (C$_1$-C$_4$)alkyl substituents on the ring carbons and optionally contains a further hetero group selected from —O—, —S—, and —NR$^5$— wherein R$^5$ is defined as above, said ring selected from the group consisting of morpholinyl, piperidinyl, piperazinyl, thiomorpholinyl, pyrazolidinyl, 1,3-oxazolidinyl, 1,3-thiazolidinyl and hexahydroazepinyl;

B represents hydrogen or N-acetyl-beta-D-2-deoxy-2-aminoglucopyranosyl;

M represents hydrogen or alpha-D-mannopyranosyl; with the proviso that when W represents a group —NR$^3$R$^4$, ureido, guanidino or a nitrogen containing 5-6 membered heterocyclic ring as defined above directly connected with the "alk" moiety through a bond with a ring nitrogen atom, the linear alkylene "alk" moiety must be of at least two carbon atoms; or a pharmaceutically acceptable addition salt thereof.

2. A compound according to claim 1 wherein Y represents hydroxy or NR¹R² wherein this group represents —HNCH(COOCH₃) (CH₂)₄ NH₂,

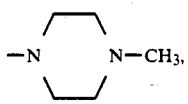

or —HN(alk)W wherein "alk" represents a linear alkylene chain of 2, 3, 4, 5, 6, 7 or 8 methylene units and W represents a group selected from —NH₂, —NHCH₃, —NHC₂H₅, —N(CH₃)₂, —N(C₂H₅)₂, and —N(CH₃)(C₂H₅).

3. A compound according to claim 1 wherein A and R¹⁶ have the same meaning when Y represents OR¹⁶.

4. A compound according to claim 3 wherein A is selected from (C₅-C₆)cycloalkyl, (C₅-C₆)cycloalkyl(C₁-C₄)alkyl, epoxy (C₃-C₆)alkyl, hydroxy(C₂-C₆)alkyl, (C₁-C₄)alkoxy (C₁-C₄)alkyl, tetrahydrooxofuryl, halo(C₂-C₅)alkyl, cyano(C₁-C₄)alkyl, phenyl(C₁-C₃)alkyl; a group (CH₂)$_s$ (CO)$_t$ R¹³ wherein s represents the integer 1, 2, 3 or 4, t represents zero or 1, R¹³ represents hydroxy, (C₁-C₄)alkoxy or a 5-10 membered heterocyclic ring selected from morpholinyl, piperidinyl, piperazinyl, pyrrolidyl, indolyl, dioxoindolyl, and oxazolidinyl: a group of formula

[(CH₂)$_s$(CO)$_t$NR¹⁴]$_u$R¹⁵ wherein one of the hydrogen atoms of a CH₂ unit may be replaced a hydroxy(C₁-C₄)alkyl group, s represents 2, 3 or 4, t represents zero or 1, u represents 1, 2, 3 or 4, R¹⁴ represents hydrogen, (C₁-C₃)alkyl, (CH₂)$_s$NH₂, (CH₂)$_s$NH (C₁-C₂)alkyl, (CH₂)$_s$—N[(C₁-C₂) alkyl]₂, wherein s represents 2, 3 or 4, and R¹⁵ represents hydrogen, (C₅-C₆)cycloalkyl, (C₁-C₃)alkyl or (CH₂)$_s$—COO(C₁-C₃)alkyl, wherein s represents 2,3 or 4.

5. A pharmaceutical composition comprising a compound of claim 1 in admixture with a pharmaceutically acceptable carrier.

6. A method of treating bacterial infections comprising administering to a patient in need thereof an antibacterially effective amount of a compound of claim 1.

* * * * *